United States Patent [19]

Inoue et al.

[11] Patent Number: 4,845,219

[45] Date of Patent: Jul. 4, 1989

[54] NITROGEN- AND SULFUR-CONTAINING LIPID COMPOUNDS THEIR PRODUCTION AND USE

[75] Inventors: Keizo Inoue, Tokyo; Hiroaki Nomura, Osaka; Tetsuya Aono, Kyoto, all of Japan

[73] Assignee: Takeda Chemical Industries, Ltd., Japan

[21] Appl. No.: 76,887

[22] Filed: Jul. 23, 1987

[30] Foreign Application Priority Data

Jul. 30, 1986 [JP] Japan .................. 61-177797
Apr. 9, 1987 [JP] Japan .................. 62-85706

[51] Int. Cl.$^4$ .................. C07D 295/08; C07D 295/10; C07C 149/10
[52] U.S. Cl. .................. 544/107; 546/331; 546/334; 546/339; 546/340; 546/248; 548/193; 548/194; 548/146; 548/574; 560/155; 560/170; 568/672; 568/678; 544/158; 544/398
[58] Field of Search .................. 544/107, 158, 398; 548/193, 194, 146, 574; 546/331, 334, 339, 340, 248; 560/155, 170; 568/672, 678

[56] References Cited

U.S. PATENT DOCUMENTS 4,426,525  1/1984  Hozumi .................. 548/112

FOREIGN PATENT DOCUMENTS 0208961  1/1987  European Pat. Off.

OTHER PUBLICATIONS

Hackh's Chemical Dictionary, 4th ed., McGraw-Hill 1972, p. 16.

*Primary Examiner*—Mary C. Lee
*Assistant Examiner*—Mary Sue Howard
*Attorney, Agent, or Firm*—Wegner & Bretschneider

[57] ABSTRACT

A compound of the general formula [I]:

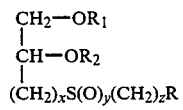

wherein $R_1$ represents a higher alkyl group or an N-(higher alkyl)carbamoyl group, $R_2$ represents a lower alkyl group, an acyl group having at least three carbon atoms, an N-(lower alkyl)carbamoyl group, an N-(lower alkyl)thiocarbamoyl group or a benzyl group, R represents a primary, secondary or tertiary amino group or a quaternary ammonium group, x is 1 or 2, y is a number of 0, 1 or 2, and z is an integer of 2–10, or a pharmaceutically acceptable salt thereof. The novel substances have both anti-tumor activity and platelet activating factor-inhibiting property, and they are effective as an anti-tumor agent without circulatory trouble.

23 Claims, No Drawings

NITROGEN- AND SULFUR-CONTAINING LIPID COMPOUNDS THEIR PRODUCTION AND USE

FIELD OF THE INVENTION

This invention relates generally to a nitrogen- and sulfur-containing lipid compound or a salt thereof which is useful as an anti-tumor agent and, more specifically, to a nitrogen- and sulfur-containing lipid compound or a salt thereof in which the nitrogen and sulfur are present in its propanediol or butanediol moiety and which exhibits a platelet activating factor-inhibiting property as well as an anti-tumor property.

DESCRIPTION OF THE PRIOR ART

There has been recently revealed a platelet activating factor (PAF) which is a phospholipid existing in mammalian bodies and which is represented by the formula [II]:

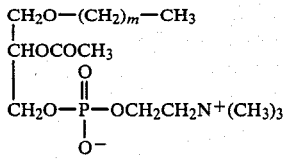

wherein m is 15 or 17. This compound [II] is known to exhibit neutrophil activating property, tissue damaging activity, blood vessel permeability enhancing activity, hypotensive activity, cardio-inhibitory activity and bronchoconstricting activity in addition to strong platelet aggregating activity.

The toxicity of the compound [II] to warm-blooded animals is very strong; e.g. the fatal dose thereof to mice is revealed to be about 50 μg/kg (i.v. dosage). Synthetic phospholipid compounds similar to the compound [II] are also known to exhibit PAF-like activity, though the activation strength varies with their chemical structures. For example, the compound disclosed in Japanese Unexamined Patent Publication No. 52-134027 and represented by the following formula [III]:

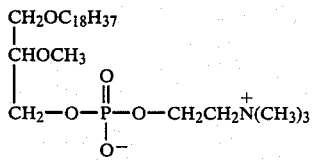

is known to have both anti-tumor activity and platelet activating property [D. J. Hanahan et al., Biochem. Biophys. Res. Commun., 99, 183(1981)]. Such a property against platelets is likely to induce heavy circulatory troubles such as cerebral thrombosis and angina pectoris. The compound [III] is also proved to exhibit hypotensive activity and local stimulating activity. These activities, which lead to side effects [W. E. Berdel et al., Anticancer Res., 1, 345(1981)], restrict the utilization thereof as a medicament.

As described in the foregoing, the PAF-like activity of synthetic phospholipids is a serious bar to development of synthetic phospholipids for use as medicament. There is a recent report by Allan Wissner et al. on the following compounds [Allan Wissner, C. A. Kohler and B. M. Goldstein, J. Med. Chem., 28, 1365(1985)]:

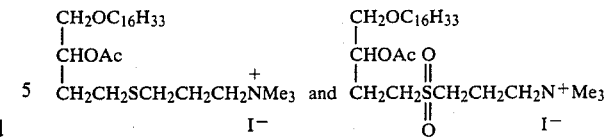

The authors referred to the effect that these compounds do not cause such platelet aggregation in $1.8 \times 10^{-4}$ M as is caused by PAF and that the hypotensive activity is reduced (details are unknown). This report, however, is silent with respect to anti-tumor activity.

Generally, synthetic phospholipid compounds, especially when they have a relatively small substituent at the 2-position, exhibit platelet aggregating activity, hypotensive activity and the like. These activities cause side effects when the phospholipid compounds are used as an anti-tumor agent. Since the amount of the compounds required for obtaining anti-tumor effect is close to the amount which causes side effects, it is difficult to use such phospholipid compounds as an anti-tumor agent.

SUMMARY OF THE INVENTION

The present inventors have made an intensive study for developing lipids which do not have the PAF-like activity but can exhibit potent anti-tumor activity. As a result, it has been found that the compounds of the formula [I] in which sulfone, sulfoxide or sulfide is substituted for the phosphate moiety of a phospholipid exhibit remarkable anti-tumor activity and do not have PAF activities such as hypotensive activity and platelet aggregating activity and that many of these compounds hinder the aggregating of platelets which is induced by PAF.

In general, aggregation of platelets is considered to play an important role in metastasis of tumor cells. Namely, there is a hypothesis that tumor cells metastasize through arrest step on the wall of blood vessels, the arrest being increased by the interaction between the tumor cells and platelets. Nowadays, many researchers have made studies to determine whether or not platelet aggregation inhibitors can prevent metastasis in tumor-bearing animals. Positive results are being collected so that the credibility of the hypothesis is being increased [Takashi Tsuruo et al., Cancer Chemother. Pharmacol., 14, 30(1985)]. According to this thought, medicaments having a platelet aggregation inhibiting activity are expected to have metastasis inhibiting activity. The sulfur containing lipid according to the present invention which exhibits both the anti-tumor activity and platelet aggregation inhibiting activity is also expected to have the metastasis inhibiting effect. The present invention has thus been made based on the findings that the compound expressed by the general formula [I] has excellent properties as an anti-tumor agent.

In accordance with the present invention there is provided a compound expressed by the following general formula [I]:

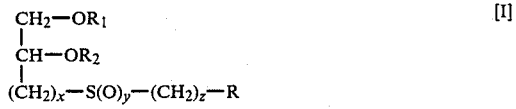

wherein $R_1$ represents a higher alkyl group or an N-(higher alkyl) carbamoyl group, $R_2$ represents a lower alkyl group, an acyl group having at least three carbon atoms, an N-(lower alkyl)carbamoyl group, an N-(lower alkyl)thiocarbamoyl group or a benzyl group, R represents a primary, secondary or tertiary amino group or a quaternary ammonium group, x is 1 or 2, y is 0, 1 or 2, and z is an integer of 2–10, or a salt thereof.

DESCRIPTION OF THE PREFERRED EMBODIMENT

The higher alkyl group referred to by the symbol $R_1$ in the general formula [I] may be, for example, a straight chain alkyl group having 14–20 carbon atoms such as tetradecyl, pentadecyl, hexadecyl, heptadecyl, octadecyl, nonadecyl or eicosyl, or a branched chain alkyl group having 14–20 carbon atoms such as 3,7,11-trimethyldodecyl, 3,7,11,15-tetramethylhexadecyl or 12-cyclohexyldodecyl. The N-(higher alkyl)carbamoyl group represented by $R_1$ may be, for example, an alkylcarbamoyl group whose alkyl moiety is the above-described higher alkyl group.

The lower alkyl group referred to by the symbol $R_2$ may be, for example, an alkyl group having 1–4 carbon atoms such as methyl, ethyl, propyl, isopropyl or butyl. Examples of the acyl group with at least 3 carbon atoms represented by the symbol $R_2$ includes alkanoyl groups such as propionyl and butyryl and an acetoacetyl group. Above all, a lower alkanoyl group with 3 or 4 carbon atoms or an acetoacetyl group is preferred. Examples of the N-(lower alkyl)carbamoyl group and the N-(lower alkyl)thiocarbamoyl group referred to by the symbol $R_2$ include N-($C_{1-4}$ alkyl)carbamoyl groups and N-($C_{1-4}$ alkyl)thiocarbamoyl groups such as methylcarbamoyl, ethylcarbamoyl, propylcarbamoyl and methylthiocarbamoyl.

The primary to tertiary amino groups referred to by the symbol R may be, for example those represented by the formula:

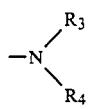

wherein $R_3$ and $R_4$ each stand independently for hydrogen or a lower alkyl group or $R_3$ and $R_4$ together with the adjacent nitrogen atom, form a cyclic amino group.

The lower alkyl group referred to by the symbols $R_3$ and $R_4$ may be a $C_1$-$C_5$ alkyl group such as methyl, ethyl, propyl, butyl or pentyl, and is preferably methyl.

Examples of the cyclic amino group include five or six membered cyclic amino groups such as pyrrolidino, piperidino, piperazino and morpholino. These groups may further have a substituent such as a $C_{1-4}$ alkyl group (e.g. methyl, ethyl, propyl or butyl), a hydroxyl group, a hydroxyethyl group, an aminoethyl group, a carbamoyl group or an ureido group.

The quaternary ammonium group referred to by the symbol R may be, for example, one represented by the formula:

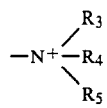

wherein $R_3$, $R_4$ and $R_5$ each stand independently for hydrogen or a lower alkyl group or $R_3$, $R_4$ and $R_5$ represent a cyclic ammonio group as follows:

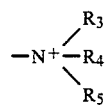

The lower alkyl group referred to by the symbol $R_3$, $R_4$ or $R_5$ may be, for example, an alkyl having 1–5 carbon atoms such as methyl, ethyl, propyl, butyl or pentyl, and is preferably methyl.

As the cyclic ammonio group, there may be mentioned pyridinio, oxazolio, thiazolio, pyridazinio, quinolinio, isoquinolinio, 1-[lower ($C_{1-4}$) alkyl]pyrrolidinio, 1-[lower($C_{1-4}$) alkyl]piperidinio, N-[lower ($C_{1-4}$) alkyl]morpholinio and 1-[lower ($C_{1-4}$) alkyl]piperazinio. These groups may further have a substituent such as a lower alkyl group having 1–4 carbon atoms such as methyl, ethyl, propyl or butyl, hydroxyl group, hydroxyethyl group, aminoethyl group, carbamoyl group or ureido group.

The compound [I], in which R is a primary, secondary or tertiary amine, may form a salt with a pharmacologically acceptable inorganic or organic acid such as hydrochloric acid, hydrobromic acid, hydroiodic acid, sulfuric acid, acetic acid, lactic acid, tartaric acid, citric acid, methanesulfonic acid, ethanesulfonic acid, benzenesulfonic acid or toluenesulfonic acid.

The compound [I], in which R is a quaternary ammonium group, may form a salt with an anion ($X^-$) of a pharmacologically acceptable inorganic or organic acid such as hydrochloric acid, hydrobromic acid, hydroiodic acid, sulfuric acid, acetic acid, lactic acid, tartaric acid, citric acid, methanesulfonic acid, ethanesulfonic acid, benzenesulfonic acid or toluenesulfonic acid. Illustrative of suitable anions are halogen ions such as chloride ion, bromide ion and iodide ion, methanesulfonate ion and p-toluenesulfonate ion.

In the compound [I] there exist two stereoisomers, i.e. R-configuration and S-configuration. Both of the isomers, mixtures thereof and a racemate are to be included within the scope of the present invention.

The compound [I] according to the present invention may be produced, for example, by a method as illustrated in Scheme I shown in the next page. The reactions involved in Scheme I are known per se.

SCHEME II

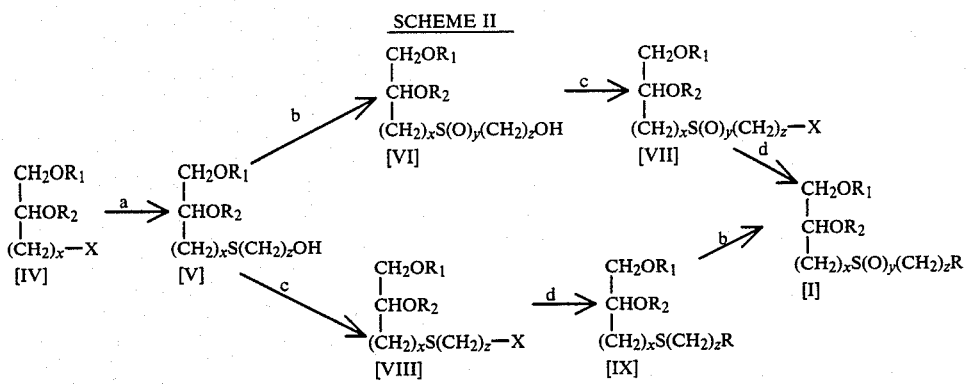

[wherein, R, $R_1$, $R_2$, $R_3$, $R_4$, $R_5$, x, y, z and X have the same meaning as above]

Step (a) is to substitute the thiolate anion of the compound [X']:

HS—(CH$_2$)$_z$OH  [X']

where z has the same meaning as above, for the group X (X is preferably halogen, methanesulfonyloxy, ethanesulfonyloxy, benzenesulfonyloxy or toluenesulfonyloxy) of the compound [IV]. Any solvent may be used in this step as long as it is inert to the reaction. However, the use of an alcohol such as methanol or ethanol or water is preferred. As the base to be used in this step, a sodium alkoxide such as sodium methoxide or sodium ethoxide, sodium hydroxide or potassium hydroxide may be suitably employed. The reaction is desirably performed at 0°–80° C. under nitrogen streams.

Step (b) involves the oxidation of a sulfide (the compound [V] or [IX]). The oxidizing agent to be used in this step is preferably a peracid such as hydrogen peroxide, peracetic acid, perbenzoic acid or m-chloroperbenzoic acid. As the solvent, water-containing acetic acid, water-containing acetone, chloroform, dichloromethane or the like is used. The reaction temperature is preferably 0°–50° C. When the oxidation is performed with an amount of the oxidizing agent of at least two moles per mole of the sulfide, a sulfone (a compound in which y=2) is obtained as product. If a sulfoxide is intended to be produced, the amount of the oxidizing agent used is preferably equimole or less.

Step (c) is to convert an alcohol into a reactive derivative. As the reactive derivatives from alcohols, there may be mentioned sulfonates and halides of alcohols. Sulfonates may be generally obtained by reacting the compound [V] or [VI] with a sulfonyl chloride such as methanesulfonyl chloride, benzenesulfonyl chloride or p-toluenesulfonyl chloride in the presence of a base. The halides may be obtained by reacting the compound [V] or [VI] with an anhydrous hydrogen halide such as hydrogen chloride or hydrogen bromide, a thionyl halide such as thionyl chloride or thionyl bromide, a phosphorus halide such as phosphorus pentachloride, phosphorus trichloride, phosphorus pentabromide or phosphorus tribromide, or phosphorus oxychloride in an inert solvent. Further, the reaction of a sulfonate ester (a compound [VII] or a compound [VIII]) with sodium bromide or sodium iodide can give the corresponding halide. The reaction in step (c) is preferably carried out at a temperature of −20° to 50° C.

In step (d) the compound [VII] or [VIII] is reacted with an amine represented by the general formula [XI] or [XII]:

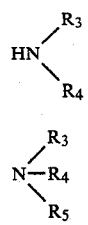

wherein $R_3$, $R_4$ and $R_5$ each have the same meaning as above, in an inert solvent such as toluene or benzene. This step is performed at a temperature of 0° to 100° C.

The steps of the scheme I have been described in the foregoing. The group represented by $R_2$ may be converted, during any desired step of the scheme I, into another group which is also represented by $R_2$. For instance, a compound in which $R_2$ is a benzyl group may be catalytically reduced into a compound in which $R_2$ is hydrogen, the hydrogen being subsequently converted into an alkylcarbamoyl or alkylthiocarbamoyl group by reaction with an alkyl isocyanate or an alkyl isothiocyanate. Alternatively, the compound wherein $R_2$ is H may be acylated by any known manner to obtain a compound in which $R_2$ is an acyl group.

A compound in which y=2, z=2 and R represents a primary secondary or tertiary amino group may also be prepared by treating the compound [VII] in a suitable solvent in the presence of a tertiary amine such as trimethylamine or pyridine at 0° C. to 80° C. to give a compound of the formula [XIII]:

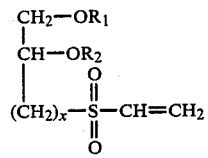

(wherein the symbols have the same meanings as above), the compound [XIII] being thereafter reacted with the compound [XI]. The reaction of the compound [XIII] with the compound [XI] may be performed in the same manner as that between the compounds [VII] and [XI].

In preparing the compound [I] in which y=0, it is not necessary to carry out the step (b).

The compound [I] in which R is a secondary or tertiary amino group or a quaternary ammonium group may also be prepared by reacting the corresponding compound [I] in which R is a primary, secondary or tertiary amine with an alkylating agent, such as a lower ($C_1$–$C_5$) alkyl halide (e.g. methyl iodide), a lower ($C_1$–$C_5$) alkyl toluenesulfonate, or a lower ($C_1$–$C_5$) alkyl methanesulfonate, in an appropriate solvent at 10°–100° C.

A salt of the compound [I] in which R is primary, secondary or tertiary amine may be prepared using, if necessary, an inorganic or organic acid, though such a compound may, in some cases, be obtained during the course of the above-described reactions.

When R is a quaternary ammonium group, the anion ($X^-$) may be replaced by another anion by means of, for example, an anion exchange resin.

The method of preparing the compound [I] or its salt described in the foregoing is a representative one and the method of preparing the compound [I] or its salt according to the present invention is not limited thereto.

The compound [I] is, in one hand, substantially free from side effects, e.g. platelet aggregation activity, hypotensive activity, blood vessel permeability enhancing activity, tissue damaging activity, which would result from platelet activating property. On the other hand, it shows an increased anti-tumor activity such as cytotoxic activity against tumor cells and, therefore, it can be dosed as a potent anti-tumor agent to tumor-bearing animals. The manner, route and amount of dosage may be suitably selected according to the subject to be dosed and symptom of the subject. The amount of dosage (as compound [I]) to tumor-bearing animals is generaly about 0.1–150 mg/kg (body weight), preferably 2–50 mg/kg. The dosage of the medicine may be daily or every 2–7 days with 1–3 times a day. It is also possible to dose the compound [I] for a long period of time by way of drip phleboclysis so as to keep the concentration of the medicine in the tissues in a required level for a long period of time.

The compound [I] and salt thereof exhibit, in addition to the above-described anti-tumor activity, PAF inhibiting activity so that it may be dosed to warm-blooded animals as an agent for preventing or curing allergic diseases such as bronchial asthma or circulatory troubles or diseases such as thrombosis, angina pectoris, cerebral thrombosis, endotoxin shock and anaphylactic shock, which might result from PAF. For this purpose, the compound [I] or salt thereof is preferably dosed in an amount of 0.2–20 mg/kg. The route or dosage and the form of the medicine to be dosed are the same as those used as in the anti-tumor agent.

The pharmaceutical composition for dosage includes an effective amount of the compound [I] or salt thereof, and a pharmacologically acceptable carrier or vehicle. The composition is processed into a form suitable for oral dosage or non-oral dosage.

As compositions for oral dosage, there may be mentioned solid or liquid agents such as tablets (inclusive of sugar-coated and film-coated tablets), pills, granules, powder, capsules (inclusive of soft capsules), syrup, emulsion and dispersion agent. These compositions may be prepared in any known manner. Examples of the carrier and vehicle customarily used in the field of pharmaceutical preparations include lactose, starch, sucrose and magnesium stearate.

The compositions for non-oral dosage may include, for example, injection medications and suppositories. Illustrative of injection medications are those for intravenous injection, hypodermic injection, intradermic injection, intramuscular injection and drip infusion. These medications may be prepared by any conventional method such as by dissolving, dispersing or emulsifying the compound [I] or salt thereof in aseptic aqueous or oily liquid customarily employed for injection medications. Examples of the aqueous liquid include physiological saline solutions and isotonic solutions containing an additive such as glucose, etc. The aqueous liquid may include a suitable solvent such as an alcohol (e.g. ethanol), a polyalcohol (e.g. propylene glycol or polyethylene glycol), or a nonionic surfactant [e.g. polysolvate 80, HCO-50 (polyoxyethylene (50 mol) adduct of hydrogenated castor oil)]. The oily liquid may be, for example, sesame oil and an oleum oil and may be used with a suitable solvent such as benzyl benzoate or benzyl alcohol. The thus prepared injection medications are generally charged into suitable ampoules. The suppository for rectal dosage may be prepared in any known manner such as by mixing the compound [I] or a salt thereof with a conventional suppository base and shaping the mixture into a suitable form.

The above compositions may further include other active ingredients as long as they do not show any undesirable interaction with the compound [I] or a salt thereof.

The compound according to the present invention and salt thereof are novel substances and exhibit both anti-tumor activity and platelet activating factor (PAF)-inhibiting activity.

EXAMPLES

Examples of the present invention will now be described below. The present invention, however, is not limited to the examples.

Examples 1–29, 41, 50–56, 59 and 61–64 provide starting material compounds for the compounds of the present invention.

EXAMPLE 1

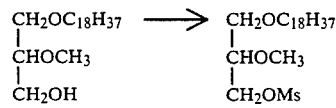

2-Methoxy-3-octadecyloxypropyl methanesulfonate

To 120 ml of dichloromethane are added 12.0 g of 2-methoxy-3-octadecyloxypropanol and 6.07 ml of triethylamine, to which 4.98 g of methanesulfonyl chloride is added dropwise with stirring under ice cooling. Thereafter, the mixture is stirred at room temperature for 2 hours to complete the reaction. The reaction mixture is then washed with water, an aqueous sodium bicarbonate solution and again water and dried over anhydrous sodium sulfate. The solvent is distilled off under reduced pressure to leave 14.6 g (100%) of the captioned compound.

IR(KBr)cm$^{-1}$: 1 2920, 2848, 1460, 1350, 1175, 1115, 1062, 820, 720.

NMR(90 MHz, CDCl₃)δ: 0.87(3H,t), 1.25(32H,m), 3.02(3H,s), 3.44(3H,s) 3.3–3.6(5H,m), 4.30(2H,m).

EXAMPLE 2

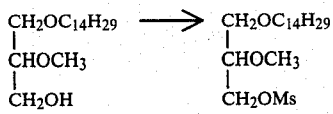

2-Methoxy-3-tetradecyloxypropyl methanesulfonate

The captioned compound is obtained from 2-methoxy-3-tetradecyloxypropanol and methanesulfonyl chloride in the same manner as that of Example 1.

IR(Neat)cm⁻¹: 2920, 2850, 1460, 1345, 1175, 1120, 965.

NMR(90 MHz, CDCl₃)δ: 0.88(3H,t), 1.0–1.7(24H,m) 3.03(3H,s), 3.47(3H,s) 3.3–3.7(5H,m), 4.33(2H,m).

EXAMPLE 3

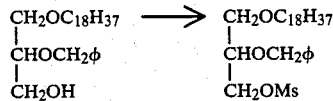

2-Methoxy-3-octadecylcarbamoyloxypropyl methanesulfonate

The captioned compound is obtained from 2-methoxy-3-octadecylcarbamoyloxypropanol and methanesulfonyl chloride in the same manner as that of Example 1.

IR(KBr)cm⁻¹: 3400, 2925, 2855, 1700, 1535, 1470, 1360, 1175, 935, 805

NMR(90 MHz, CDCl₃)δ: 0.87(3H,t), 1.1–1.7(32H,m) 3.04(3H,s), 3.47(3H,s) 3.15(2H,m), 3.67(1H,m), 4.1–4.4(4H,m), 4.8(1H).

EXAMPLE 4

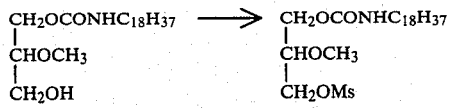

2-Benzyloxy-3-octadecyloxypropyl methanesulfonate

The captioned compound is obtained from 2-benzyloxy-3-octadecyloxypropanol and methanesulfonyl chloride in the same manner as that of Example 1.

IR(Neat)cm⁻¹: 2930, 2855, 1465, 1355, 1175, 1110, 965 910.

NMR(90 MHz, CDCl₃)δ: 0.87(3H,t), 1.25(32H,m) 2.95(3H,s), 3.3–3.65(4H,m), 3.80(1H,q), 4.33(2H,t). 4.68(2H,s), 7.36(5H,m).

EXAMPLE 5

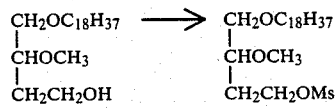

3-methoxy-4-octadecyloxybutyl methanesulfonate

The captioned compound is obtained from 3-methoxy-4-octadecyloxybutanol and methanesulfonyl chloride in the manner as that of Example 1.

IR(KBr)cm⁻¹: 2925, 2850, 1470, 1355, 1175, 982.

NMR(90 MHz, CDCl₃)δ: 0.87(3H,t), 1.25 (32H,m), 1.93(2H,m), 2.99(3H,s) 3.3–3.55(5H,m), 3.40(3H,s) 4.33(2H,t).

EXAMPLE 6

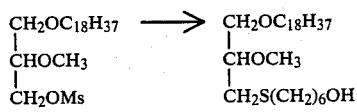

2-Methoxy-3-octadecyloxypropyl 6-hydroxyhexyl sulfide

To 14 ml of a methanol solution of sodium methoxide (1M solution) are added 2.04 g of 6-mercaptohexanol and 0.24 g of sodium borohydride, to which a THF (20 ml) solution containing 2.18 g of 2-methoxy-3-octadecyloxypropyl methanesulfonate is added dropwise under nitrogen streams with stirring. The mixture is stirred at room temperature for 20 hours and then at 40° C. for 1 hour. After the addition of water, the mixture is extracted with ethyl acetate. The extracted layer is washed with water, dried and concentrated under reduced pressures to obtain an oily product. Purification of the oily product by silica gel column chromatography gives 2.31 g of the captioned compound.

IR(Neat)cm⁻¹: 3350, 2920, 2850, 1460, 1120.

NMR(90 MHz, CDCl₃)δ: 0.86(3H,t), 1.2–1.8 (41H,m), 2.53–2.72(4H,m), 3.37–4.07(7H,m) 3.76(3H,s).

EXAMPLE 7

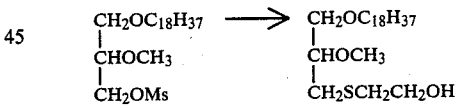

2-methoxy-3-octadecyloxypropyl 2-hydroxyethyl sulfide

The captioned compound is obtained from 2-methoxy-3-octadecyloxypropyl methanesulfonate and 2-mercaptoethanol in the same manner as that of Example 6.

IR(Neat)cm⁻¹: 1 3450, 2920, 2850, 1460, 1285, 1115.

NMR(90 MHz, CDCl₃)δ: 0.87(3H,t), 1.2–1.8 (33H,m), 2.63–2.79(4H,m), 3.37–3.87(7H,m), 3.44(3H,s).

EXAMPLE 8

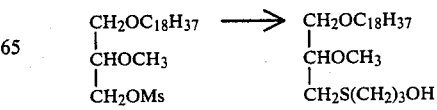

2-methoxy-3-octadecyloxypropyl 3-hydroxypropyl sulfide

The captioned compound is obtained from 2-methoxy-3-octadecyloxypropyl methanesulfonate and 3-mercaptopropanol in the same manner as that of Example 6.

IR(Neat)cm$^{-1}$: 3380, 2920, 2850, 1462, 1115.

NMR(90 MHz, CDCl$_3$)δ: 0.87(3H,t), 1.25(32H,m), 1.88(2H,m), 2.70(4H,m), 3.43(3H,s), 3.36-3.6(5H,m), 3.76(2H,m).

EXAMPLE 9

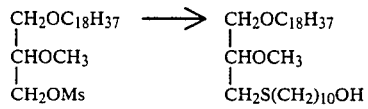

2-methoxy-3-octadecyloxypropyl 10-hydroxydecyl sulfide

The captioned compound is obtained from 2-methoxy-3-octadecyloxypropyl methanesulfonate and 10-mercaptodecanol in the same manner as that of Example 6.

IR(Neat)cm$^{-1}$: 3400, 2920, 2850, 1460, 1115.

NMR(90 MHz, CDCl$_3$)δ: 0.87(3H,t), 1.1-1.7(49H,m), 2.46-2.67(4H,m), 3.3-3.7(7H,m), 3.42(3H,s).

EXAMPLE 10

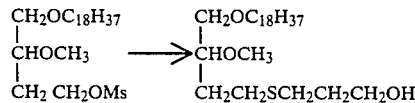

3-methoxy-4-octadecyloxybutyl 3-hydroxypropyl sulfide

The captioned compound is obtained from 3-methoxy-4-octadecyloxybutyl methanesulfonate and 3-mercaptopropanol in the same manner as that of Example 6.

IR(KBr)cm$^{-1}$: 3390, 2925, 2850, 1460, 1365, 1115.

NMR(90 MHz, CDCl$_3$)δ: 0.87(3H,t), 1.25-2.0(36H,m), 2.63(4H,m), 3.41(3H,s), 3.33-3.55(5H,m), 3.77(2H,m).

EXAMPLE 11

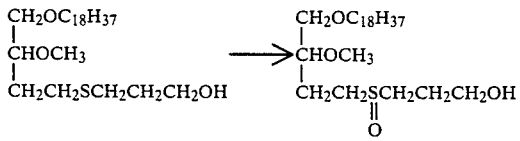

3-Hydroxypropyl 3-methoxy-4-octadecyloxybutyl sulfoxide

In 20 ml of dichloromethane is dissolved 1.52 g of 3-methoxy-4-octadecyloxybutyl 3-hydroxypropyl sulfide, to which a solution of 0.61 g of m-chloroperbenzoic acid in 8 ml of dichloromethane is added dropwise with stirring under ice cooling. Thereafter, the mixture is stirred at room temperature for 30 minutes to complete the reaction. The reaction mixture is then washed with an aqueous sodium bisulfite solution, an aqueous sodium bicarbonate solution and then water and dried. The solvent is distilled off under reduced pressure and the residue is purified by silica gel column chromatography to obtain 1.46 g of the captioned compound.

IR(KBr)cm$^{-1}$: 3420, 2920, 2850, 1650, 1465, 1380, 1130, 1060, 1000.

NMR(90 MHz, CDCl$_3$)δ: 0.87(3H,t), 1.25(32H,m), 1.8-2.23(4H,m), 2.7-3.1(4H,m), 3.40(3H,s), 3.3-3.5(5H,m), 3.75(2H).

EXAMPLE 12

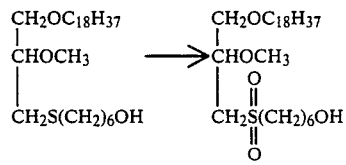

6-Hydroxyhexyl 2-methoxy-3-octadecyloxypropyl sulfone

In 50 ml of dichloromethane is dissolved 2.3 g of 2-methoxy-3-octadecyloxypropyl 6-hydroxyhexyl sulfide, to which 3.0 g of m-chloroperbenzoic acid are added little by little with stirring at 20° C. Thereafter, the mixture is stirred at room temperature for 30 minutes and the deposites are filtered off. The filtrate is then washed with an aqueous sodium bisulfite solution and is concentrated under reduced pressures. The concentrate is dissolved in ethyl acetate and washed with an aqueous sodium bicarbonate solution and water and is dried. The solvent is distilled off under reduced pressure and the residue is purified by silica gel column chromatography to obtain 1.85 g of the captioned compound.

IR(KBr)cm$^{-1}$: 3400, 2920, 2850, 1460, 1280, 1115.

NMR(90 MHz, CDCl$_3$)δ: 0.87(3H,t), 1.2-2.0(41H,m), 2.93-3.7(10H,m), 3.77(3H,s), 3.7-4.03(1H,m).

EXAMPLE 13

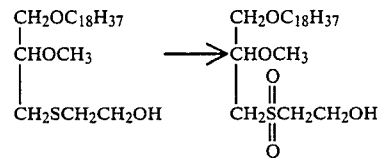

2-Hydroxyethyl 2-methoxy-3-octadecyloxypropyl sulfone

The captioned compound is obtained in the same manner as that of Example 12 from 2-methoxy-3-octadecyloxypropyl 2-hydroxyethyl sulfide and m-chloroperbenzoic acid.

IR(KBr)cm$^{-1}$: 3450, 2920, 2850, 1460, 1280, 1120.

NMR(90 MHz, CDCl$_3$)δ: 0.87(3H,t), 1.2-1.7(32H,m), 2.79(1H,t), 3.0-4.2(11H,m), 3.43(3H,s).

EXAMPLE 14

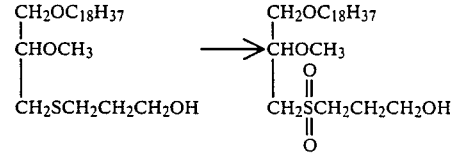

3-Hydroxypropyl 2-methoxy-3-octadecyloxypropyl sulfone

The captioned compound is obtained in the same manner as that of Example 12 from 2-methoxy-3-octadecyloxypropyl 3-hydroxypropyl sulfide and m-chloroperbenzoic acid.

IR(KBr)cm$^{-1}$: 3450, 2925, 2850, 1468, 1298, 1120, 1065.

NMR(90 MHz, CDCl$_3$)δ: 0.87(3H,t), 1.25(32H,m), 2.09(2H,m), 3.43(3H,s), 3.1–3.55(9H,m), 3.65–4.0(2H,m).

EXAMPLE 15

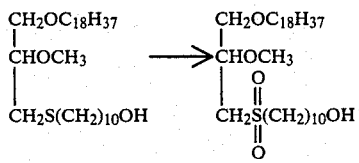

10-Hydroxydecyl 2-methoxy-3-octadecyloxypropyl sulfone

The captioned compound is obtained in the same manner as that of Example 12 from 2-methoxy-3-octadecyloxypropyl 10-hydroxydecyl sulfide and m-chloroperbenzoic acid.

IR(KBr)cm$^{-1}$: 3400, 2920, 2850, 1465, 1225.

NMR(90 MHz, CDCl$_3$)δ: 0.87(3H,t), 1.2–2.0(49H,m), 2.97–3.8(10H,m), 3.44(3H,s), 3.8–4.1(1H,m).

EXAMPLE 16

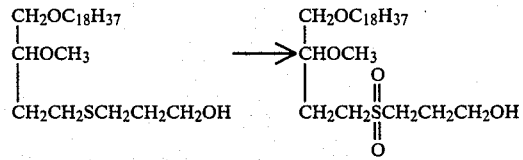

3-Hydroxypropyl 3-methoxy-4-octadecyloxybutyl sulfone

The captioned compound is obtained in the same manner as that of Example 12 from 3-methoxy-4-octadecyloxybutyl 3-hydroxypropyl sulfide and m-chloroperbenzoic acid.

IR(KBr)cm$^{-1}$: 3390, 2925, 2850, 1460, 1365, 1115.

NMR(90 MHz, CDCl$_3$)δ: 0.87(3H,t), 1.25–2.0(36H,m), 2.65(4H,m), 3.41(3H,s), 3.33–3.55(5H,m), 3.77(2H,m).

EXAMPLE 17

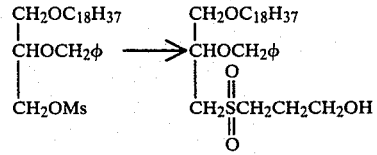

2-Benzyloxy-3-octadecyloxypropyl 3-hydroxypropyl sulfone

To 30 ml of a methanol solution containing sodium methoxide (1 M solution) are added 2.94 g of 3-mercaptopropanol and 0.59 g of sodium borohydride, to which a solution of 4.1 g of 2-benzyloxy-3-octadecyloxypropyl methanesulfonate in 50 ml of THF is added dropwise at room temperature with stirring under nitrogen streams. After the resulting mixture is stirred at room temperature for 23 hours and then at 50° C. for 2 hours, hydrochloric acid is added to the mixture to acidify. Then, the methanol is distilled off under reduced pressure and the residue is extracted with hexane. The extract is washed with water, dried and concentrated to obtain 3.97 g of crude 2-benzyloxy-oxy-3-octadecyloxypropyl 3-hydroxypropyl sulfide. The crude sulfide is dissolved in 50 ml of dichloromethane, to which 7.9 g of meta-chloroperbenzoic acid is added little by little with stirring at room temperature. Thereafter, the mixture is stirred at room temperature for 30 minutes and the undissolved substances are filtered off. The filtrate is then washed with an aqueous sodium bisulfite solution, an aqueous sodium bicarbonate solution and water, and is dried. The solvent is distilled off under reduced pressure and the residue is purified by silica gel column chromatography to obtain 2.0 g of the captioned compound.

IR(KBr)cm$^{-1}$: 2920, 2850, 1465, 1295, 1120, 1060.

NMR(90 MHz, CDCl$_3$)δ: 0.87(3H,t), 1.25(32H,m), 1.85–2.15(2H,m), 3.05–3.75(10H,m), 4.1–4.35(1H,m), 4.65(2H,m), 7.33(5H).

EXAMPLE 18

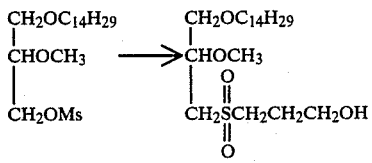

3-Hydroxypropyl 2-methoxy-3-tetradecyloxypropyl sulfone

The captioned compound is obtained in the same manner as that of Example 17 from 2-methoxy-3-tetradecyloxypropyl methanesulfonate, 3-mercaptopropanol and m-chloroperbenzoic acid.

IR(KBr)cm$^{-1}$: 3400, 2925, 2850, 1470, 1300, 1125, 1115.

NMR(90 MHz, CDCl$_3$)δ: 0.87(3H,t), 1.0–1.6(24H,m), 1.95–2.2(2H,m), 3.43(3H,s), 3.1–3.6(9H,m), 3.65–3.9(2H,m).

EXAMPLE 19

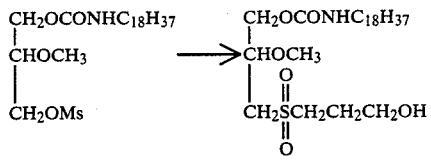

3-Hydroxypropyl 2-methoxy-3-octadecylcarbamoyloxypropyl sulfone

The captioned compound is obtained in the same manner as that of Example 17 from 2-methoxy-3-octadecylcarbamoyloxypropyl methanesulfonate, 3-mercaptopropanol and m-chloroperbenzoic acid.

IR(KBr)cm$^{-1}$: 3350, 2920, 2850, 1695, 1530, 1465, 1255, 1110.

NMR(90 MHz, CDCl$_3$)δ: 0.87(3H,t), 1.1–1.6(32H,m), 1.95–2.25(2H,m), 2.9–3.35(7H,m), 3.47(3H,s), 3.77(2H,t), 4.2(2H,m), 4.8(1H).

EXAMPLE 20

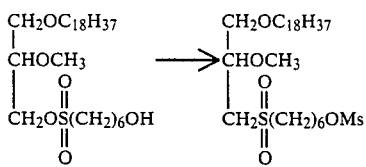

6-Mesyloxyhexyl 2-methoxy-3-octadecyloxypropyl sulfone

In 30 ml of dichloromethane are dissolved 1.77 g of 6-hydroxyhexyl 2-methoxy-3-octadecyloxypropyl sulfone and 0.64 ml of triethylamine, to which 0.35 ml of methanesulfonyl chloride is added dropwise with stirring at room temperature. Thereafter, the mixture is stirred at room temperature for 2 hours and the solvent is distilled off under reduced pressure. The residue is dissolved in ethyl acetate and washed successively with dilute hydrochloric acid, water, an aqueous sodium bicarbonate solution and water. After drying, the solvent is distilled off to leave 1.98 g of the captioned compound.

IR(KBr)cm$^{-1}$: 2920, 2850, 1460, 1350, 1285, 1160, 1125, 1110.

NMR(90 MHz, CDCl$_3$)δ: 0.87(3H,t), 1.2–2.0(40H,m), 2.98(3H,s), 3.0–3.6(8H,m), 3.43(3H,s), 3.7–4.1(1H,m), 4.22(2H,t).

EXAMPLE 21

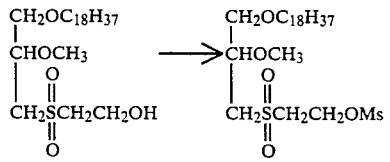

2-Mesyloxyethyl 2-methoxy-3-octadecyloxypropyl sulfon

The captioned compound is obtained in the same manner as that of Example 20 from 2-hydroxyethyl 2-methoxy-3-octadecyl-oxypropyl sulfone and methanesulfonyl chloride.

IR(KBr)cm$^{-1}$: 2920, 2850, 1460, 1350, 1295, 1170, 1125, 1110.

NMR(90 MHz, CDCl$_3$)δ: 0.87(3H,t), 1.2–1.7(32H,m), 3.05(3H,s), 3.16–3.67(8H,m), 3.43(3H,s), 3.7–4.0(1H,m), 4.61(2H,t)

EXAMPLE 22

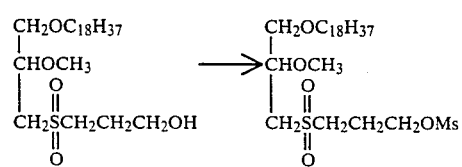

3-Mesyloxypropyl 2-methoxy-3-octadecyloxypropyl sulfone

The captioned compound is obtained in the same manner as that of Example 20 from 3-hydroxypropyl 2-methoxy-3-octadecyloxypropyl sulfone and methanesulfonyl chloride.

IR(KBr)cm$^{-1}$: 2920, 2850, 1465, 1350, 1300, 1172, 1120, 965, 925.

NMR(90 MHz, CDCl$_3$)δ: 0.87(3H,t), 1.25(32H,m), 2.30(2H,m), 3.01(3H,s), 3.05–3.65(8H,m), 3.43(3H,s), 3.90(1H,m), 4.37(2H,t).

EXAMPLE 23

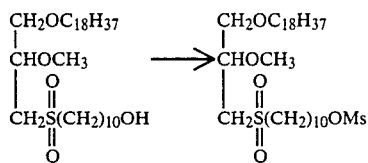

10-Mesyloxydecyl 2-methoxy-3-octadecyloxypropyl sulfone

The captioned compound is obtained in the same manner as that of Example 20 from 10-hydroxydecyl 2-methoxy-3-octadecyloxypropyl sulfone and methanesulfonyl chloride.

IR(KBr)cm$^{-1}$: 2920, 2850, 1465, 1350, 1170, 1120.

NMR(90MHz, CDCl$_3$)δ: 0.87(3H,t), 1,2–2.0(48H,m), 2.98(3H,s), 3.0–3.6(8H,m), 3.43(3H,s), 3.8–4.1(1H,m), 4.22(2H,t).

EXAMPLE 24

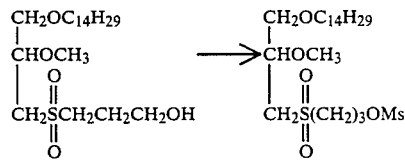

3-Mesyloxypropyl 2-methoxy-3-tetradecyloxypropyl sulfone

The captioned compound is obtained in the same manner as that of Example 20 from 3-hydroxypropyl 2-methoxy-3-tetradecyloxypropyl sulfone and methanesulfonyl chloride.

IR(Neat)cm$^{-1}$: 2920, 2850, 1460, 1350, 1310, 1170, 1115.

NMR(90 MHz, CDCl$_3$)δ: 0.87(3H,t), 1.1–1.7(24H,m), 2.2–2.5(2H,m), 3.03(3H,s), 3.44(3H,s), 3.1–3.6(8H,m), 3.8–4.1(1H,m), 4.38(2H,t).

EXAMPLE 25

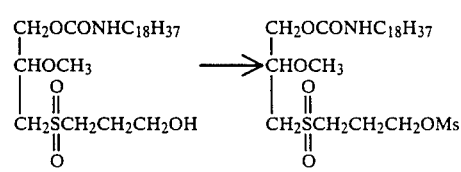

3-Mesyloxypropyl 2-methoxy-3-octadecylcarbamoyloxypropyl sulfone

The captioned compound is obtained in the same manner as that of Example 20 from 3-hydroxypropyl 2-methoxy-3octadecylcarbamoyloxypropyl sulfone and methanesulfonyl chloride.

IR(KBr)cm$^{-1}$: 3350, 2920, 2850, 1700, 1535, 1465, 1350, 1170.

NMR(90 MHz, CDCl$_3$)δ: 0.87(3H,t), 1.1–1.7(32H,m), 2.13–2.46(2H,m), 3.01(3H,s), 3.44(3H,s), 3.1–3.4(6H,m), 3.8–4.3(3H,m), 4.38(2H,t).

EXAMPLE 26

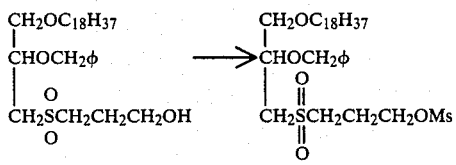

2-Benzyloxy-3-octadecyloxypropyl 3-mesyloxypropyl sulfone

The captioned compound is obtained in the same manner as that of Example 20 from 2-benzyloxy-3-octadecyloxypropyl 3-hydroxypropyl sulfone and methanesulfonyl chloride.

IR(Neat)cm$^{-1}$: 2920, 2850, 1465, 1350, 1300, 1175, 1120, 920, 730.

NMR(90 MHz, CDCl$_3$)δ: 0.87(3H,t), 1.28(32H,m), 2.1–2.36(2H,m), 2.91(3H,s), 3.0–3.55(9H,m), 4.20(2H,t), 4.65(2H,dd), 7.34(5H).

EXAMPLE 27

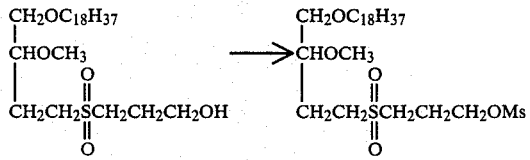

3-Mesyloxypropyl 3-methoxy-4-octadecyloxybutyl sulfone

The captioned compound is obtained in the same manner as that of Example 20 from 3-hydroxypropyl 3-methoxy-4-octadecyloxybutyl sulfone and methanesulfonyl chloride.

IR(Neat)cm$^{-1}$: 2925, 2850, 1465, 1350, 1270, 1170, 1120.

NMR(90 MHz, CDCl$_3$)δ: 0.87(3H,t), 1.25–1.6(32H,m), 1.9–2.4(4H,m), 3.0(3H,s), 2.9–3.3(4H,m), 3.3–3.6(5H,m), 3.37(3H,s), 4.38(2H,t).

EXAMPLE 28

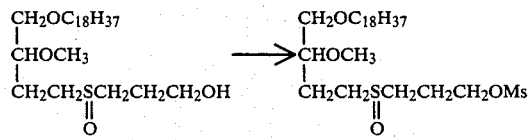

3-Mesyloxypropyl 3-methoxy-4-octadecyloxybutyl sulfoxide

The captioned compound is obtained in the same manner as that of Example 20 from 3-hydroxypropyl 3-methoxy-4-octadecyloxybutyl sulfoxide and methanesulfonyl chloride.

NMR(90 MHz, CDCl$_3$)δ: 0.87(3H,t), 1.25(32H,m), 1.9–2.43(4H,m), 2.85–3.55(4H,m), 3.03(3H,s), 3.40(3H,s), 3.3–3.6(5H,m), 4.40(2H,t).

EXAMPLE 29

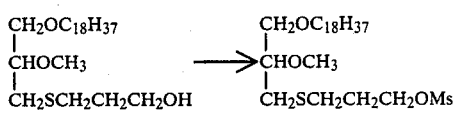

3-Mesyloxypropyl 2-methoxy-3-octadecyloxypropyl sulfide

The captioned compound is obtained in the same manner as that of Example 20 from 3-hydroxypropyl 2-methoxy-3-octadecyloxypropyl sulfide and methanesulfonyl chloride.

IR(KBr)cm$^{-1}$: 2920, 2850, 1460, 1350, 1170, 1120.

NMR(90 MHz, CDCl$_3$)δ: 0.87(3H,t), 1.2–1.8(32H,m), 1.9–2.2(2H,m), 2.62–2.77(4H,m), 2.98(3H,s), 3.3–3.6(4H,m), 3.42(3H,s), 4.33(3H,t).

EXAMPLE 30

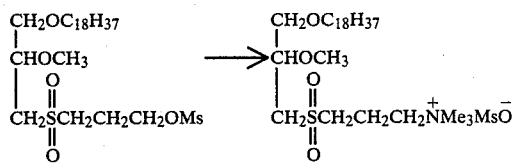

3-[(2-methoxy-3-octadecyloxypropyl)sulfonyl]propyl-trimethylammonium mesylate

In 10 ml of toluene containing 2.0 g of trimethylamine are dissolved 1.45 g of 3-mesyloxypropyl 2-methoxy-3-octadecyloxypropyl sulfone and the solution is stirred at room temperature for 3 days. The reaction solution is then concentrated to dryness and the residue is purified by silica gel column chromatography to give 1.04 g of the captioned compound.

IR(KBr)cm$^{-1}$: 3420, 2920, 2850, 1462, 1285, 1202, 1190, 1202, 1190, 1110, 1055.

NMR(90 MHz, CDCl$_3$)δ: 0.87(3H,t), 1.25(32H,m), 2.33(2H,m), 2.70(3H,s), 3.32(9H,s), 3.45(3H,s), 3.15–3.6(11H,m), 3.7–4.0(3H,m).

EXAMPLE 31

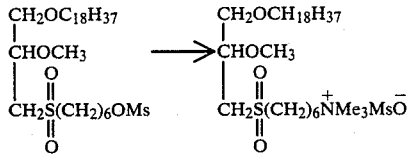

6-[(2-methoxy-3-octadecyloxypropyl)sulfonyl]hexyl-trimethylammonium mesylate

The captioned compound is obtained in the same manner as that of Example 30 from 6-mesyloxyhexyl 2-methoxy-3-octadecyloxypropyl sulfone and trimethylamine.

IR(KBr)cm$^{-1}$: 3420, 2920, 2850, 1460, 1280, 1200, 1120, 1055.

NMR(90 MHz, CDCl$_3$)δ: 0.87(3H,t), 1.2–2.0(40H,m), 2.72(3H,s), 2.8–3.7(10H,m), 3.33(9H,s), 3.46(3H,s), 3.7–4.05(1H,m).

EXAMPLE 32

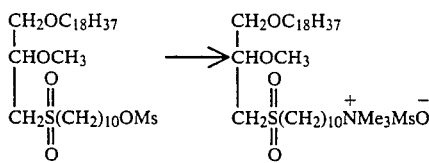

10-[(2-methoxy-3-octadecyloxypropyl)sulfonyl]decyl-trimethylammonium mesylate

The captioned compound is obtained in the same manner as that of Example 30 from 10-mesyloxydecyl 2-methoxy-3-octadecyloxypropyl sulfone and trimethylamine.

IR(KBr)cm$^{-1}$: 3400, 2920, 2850, 1460, 1285, 1190, 1115, 1050.

NMR(90 MHz, CDCl$_3$)δ: 0.87(3H,t), 1.1–2.0(48H,m), 2.70(3H,s), 2.9–3.6(10H,m), 3.30(9H,s), 3.43(3H,s), 3.7–4.0(1H,m).

EXAMPLE 33

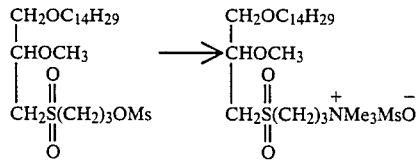

3-[(2-methoxy-3-tetradecyloxypropyl)sulfonyl]propyl-trimethylammonium mesylate

The captioned compound is obtained in the same manner as that of Example 30 from 3-mesyloxypropyl 2-methoxy-3-tetradecyloxypropyl sulfone and trimethylamine.

IR(KBr)cm$^{-1}$: 3420, 2920, 2850, 1462, 1290, 1210, 1190, 1110, 1055.

NMR(90MHz, CDCl$_3$)δ: 0.87(3H,t), 1.1–1.8(24H,m), 2.2–2.6(2H,m), 2.70(3H,s), 3.2–3.6(8H,m), 3.33(9H,s), 3.43(3H,s), 3.7–4.1(3H,m).

EXAMPLE 34

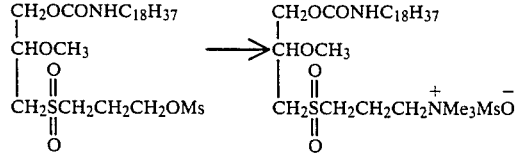

3-[(2-methoxy-3-octadecylcarbamoyloxypropyl)sulfonyl]propyltrimethylammonium mesylate The captioned compound is obtained in the same manner as that of Example 30 from 3-mesyloxypropyl 2-methoxy-3-octadecylcarbamoyloxypropyl sulfone and trimethylamine.

IR(KBr)cm$^{-1}$: 3420, 2920, 2850, 1700, 1530, 1462, 1290, 1190, 1110, 1050.

NMR(90 MHz, CDCl$_3$)δ: 0.87(3H,t), 1.1–1.8(32H,m), 2.2–2.6(2H,m), 3.0–4.4(11H,m), 2.67(3H,s), 3.32(9H,s), 3.43(3H,s), 5.84(1H).

EXAMPLE 35

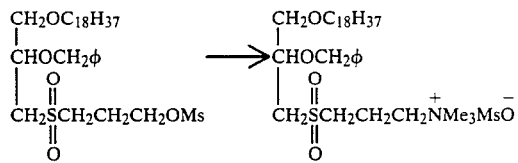

3-[(2-benzyloxy-3-octadecyloxypropyl)sulfonyl]propyl-trimethylammonium mesylate

The captioned compound is obtained in the same manner as that of Example 30 from 2-benzyloxy-3-octadecyloxypropyl 3-mesyloxypropyl sulfone and trimethylamine.

IR(KBr)cm$^{-1}$: 2920, 2850, 1465, 1285, 1210, 1190, 1055, 1035.

NMR(90 MHz, CDCl$_3$)δ: 0.87(3H,t), 1.25(32H,m), 2.05–2.45(2H,m), 2.68(3H,s), 3.17(9H,s), 3.1–3.7(10H,m), 4.2(1H), 4.67(2H,dd), 7.34(5H).

EXAMPLE 36

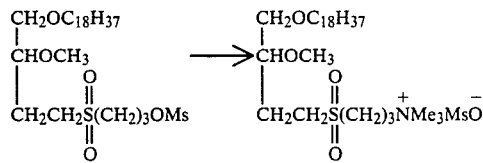

3-[(3-methoxy-4-octadecyloxybutyl)sulfonyl]propyl-trimethylammonium mesylate

The captioned compound is obtained in the same manner as that of Example 30 from 3-mesyloxypropyl 3-methoxy-4-octadecyloxybutyl sulfone and trimethylamine.

IR(KBr)cm$^{-1}$: 3420, 2920, 2850, 1465, 1280, 1200, 1190, 1125, 1060.

NMR(90 MHz, CDCl$_3$)δ: 0.87(3H,t), 1.25–1.7(32H,m), 2.03(2H,m), 2.4(2H,m), 2.71(3H,s), 2.9–3.55(9H,m), 3.31(9H,s), 3.40(3H,s), 3.65–3.9(2H,m).

EXAMPLE 37

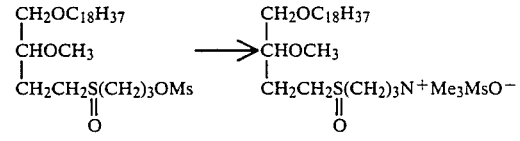

3-[(3-methoxy-4-octadecyloxybutyl)sulfinyl]propyl-trimethylammonium mesylate

The captioned compound is obtained in the same manner as that of Example 30 from 3-mesyloxypropyl 3-methoxy-4-octadecyloxybutyl sulfoxide and trimethylamine.

IR(KBr)cm$^{-1}$: 3410, 2920, 2850, 1630, 1465, 1200, 1192, 1058.

NMR(90 MHz, CDCl$_3$)δ: 0.87(3Hgt), 1.25(32H,m), 1.97(2H,m), 2.35(2H,m), 2.71(3H,s), 3.31(9H,s), 3.40(3H,s), 3.3–3.65(5H,m), 3.6–3.9(2H,m), 2.85–3.15(4H,m).

EXAMPLE 38

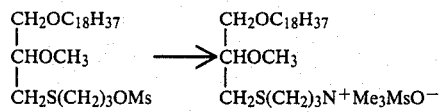

3-[(2-methoxy-3-octadecyloxypropyl)thio]propyltrimethylammonium mesylate

The captioned compound is obtained in the same manner as that of Example 30 from 3-mesyloxypropyl 2-methoxy-3-octadecyloxypropyl sulfide and trimethylamine.

IR(KBr)cm$^{-1}$: 3420, 2920, 2850, 1465, 1200, 1120, 1055.

NMR(90 MHz, CDCl$_3$) δ: 0.87(3H,t), 1.1–1.7(32H,m), 1.9–2.4(2H,m), 2.6–3.0(4H,m), 2.70(3H,s), 3.33(9H,s), 3.1–3.9(7H,m), 3.41(3H,s).

EXAMPLE 39

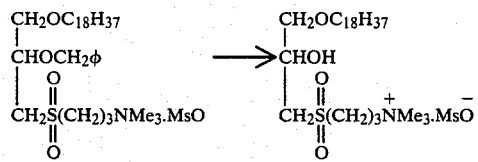

3-[(2-hydroxy-3-octadecyloxypropyl)sulfonyl]propyltrimethylammonium mesylate

Into a mixed solvent consisting of 50 ml of acetic acid and 5 ml of water is dissolved 1.4 g of 3-[(2-benzyloxy-3-octadecyloxypropyl)sulfonyl]propyltrimethylammonium mesylate and the solution is shaked in the presence of palladiumcarbon under hydrogen streams. The catalyst is then removed by filtration and the filtrate is concentrated. The resulting residue is treated with acetone to give 1.07 g of the captioned compound as powder.

IR(KBr)cm$^{-1}$: 2920, 2850, 1465, 1290, 1190, 1125, 1060.

NMR(90 MHz, CDCl$_3$) δ: 0.87(3H,t), 1.25(32H,m), 2.2–2.55(2H,m), 2.71(3H,s), 3.24(9H,s), 3.0–3.8(11H,m), 4.25(1H,s).

EXAMPLE 40

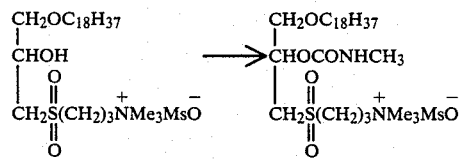

3-[(2-methylcarbamoyloxy-3-octadecyloxypropyl)sulfonyl]propyltrimethylammonium mesylate Into 6 ml of chloroform are added 1.4 g of 3-[(2-hydroxy-3-octadecyloxypropyl)sulfonyl]propyltrimethylammonium mesylate, 1 ml of methyl isocyanate and 1 ml of trimethylamine and the mixture is shaked overnight at room temperature. The reaction mixture is concentrated under reduced pressure and the residue is purified by silica gel column chromatography to give 0.2 of the captioned IR(KBr)cm$^{-1}$: 2920, 2850, 1720, 1630, 1462, 1290, 1190, 1120, 1052.

NMR(90 MHz, CDCl$_3$) δ: 0.87(3H,t), 1.25(32H,m), 2.35(2H,m), 2.73(3H,s), 2.7–2.8(3H), 3.0–4.1(10H,m), 2.88(9H,s), 5.23(1H,m), 6.77(1H,br.).

EXAMPLE 41

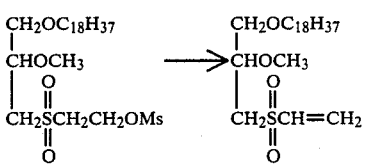

2-Methoxy-3-octadecyloxypropyl vinyl sulfone

Into 10 ml of toluene containing 2 g of trimethylamine is dissolved 1.0 g of 2-mesyloxyethyl 2-methoxy-3-octadecyloxypropyl sulfone and the solution is stirred at room temperature for 6 hours. Then 30 ml of hexane is added to the mixture and precipitates are removed by filtration. The filtrate is concentrated to give 0.6 g of the captioned compound as colorless crystals (m.p.47°–49° C.).

IR(KBr)cm$^{-1}$: 2920, 2850, 1460, 1290, 1110.

NMR(90 MHz, CDCl$_3$) δ: 0.87(3H,t), 1.1–1.6(32H,m), 3.26(2H,t), 3.40(3H,s), 3.34–3.56(4H,m), 3.67–4.0(1H,m), 6.02(1H,d), 6.34(1H,d), 6.72(1H,dd).

EXAMPLE 42

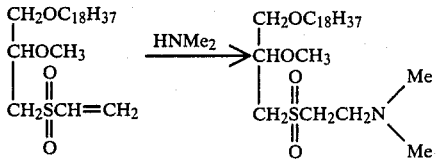

2-[(2-Methoxy-3-octadecyloxypropyl)sulfonyl]ethyldimethylamine

In 6 ml of toluene containing 1.2 g of dimethylamine is dissolved 618 mg of 2-methoxy-3-octadecyloxypropyl vinyl sulfone and the solution is stirred at room temperature for 1 hour. Then the reaction mixture is concentrated under reduced pressure to obtain 680 mg of the captioned compound as an oily substance. A hydrochloride of this compound has a melting point of 78°–80° C.

IR(KBr)cm$^{-1}$: 2930, 2850, 2570, 2450, 1470, 1300, 1240, 1220.

NMR(90 MHz, CDCl$_3$) δ: 0.87(3H,t), 1.23(32H,m), 2.8(6H,br.s), 3.2–4.0(11H,m), 3.47(3H,s), 13.2(1H).

EXAMPLE 43

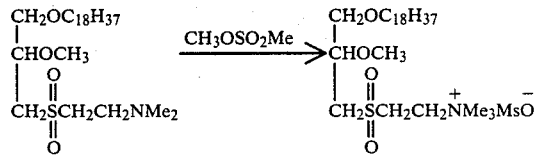

2-[(2-Methoxy-3-octadecyloxypropyl)sulfonyl]ethyl-trimethylammonium mesylate

In 10 ml of chloroform are dissolved 0.48 g of 2-[(2-methoxy-3-octadecyloxypropyl)sulfonyl]ethyldimethylamine and 1 g of methyl methanesulfonate and the solution is stirred at 70° C. for 5 hours. Then the reaction mixture is concentrated under reduced pressure and the residue is crystallized from chloroform and ether to give 417 mg of the captioned compound.

IR(KBr)cm$^{-1}$: 3420, 2920, 2850, 1480, 1460, 1320, 1190, 1115, 1040.

NMR(90 MHz, CDCl$_3$) δ: 0.87(3H,t), 1.23(32H,m), 2.69(3H,s), 3.3–4.1(11H,m), 3.39(9H,s), 3.47(3H,s).

EXAMPLE 44

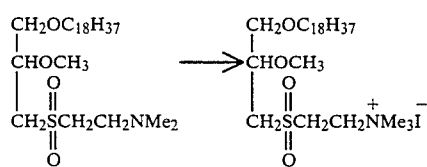

2-[(2-Methoxy-3-octadecyloxypropyl)sulfonyl]ethyl-trimethylammonium iodide

In 5 ml of ether is dissolved 0.24 g of 2-[(2-methoxy-3-octadecyloxypropyl)sulfonyl]ethyldimethylamine to which is added 1 ml of methyl iodide. The solution is then stirred at room temperature for 2 days. The reaction liquid is concentrated under reduced pressure and the residue is treated with methanol to give 275 mg of the captioned compound as powder.

IR(KBr)cm$^{-1}$: 2920, 2850, 1470, 1320, 1130, 1110.

NMR(90 MHz, d$_6$-DMSO) δ: 0.85(3H,t), 1.22(32H,m), 3.11(9H,s), 3.2–3.9(11H,m), 3.37(3H,s).

EXAMPLE 45

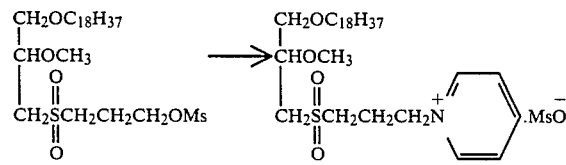

N[3-((2-Methoxy-3-octadecyloxypropyl)sulfony)-propyl]pyridinium mesylate In 5 ml of pyridine is dissolved 1.0 g of 3-mesyloxypropyl 2-methoxy-3-octadecyloxypropyl sulfone and the solution is stirred at 70° C. for 14 hours. The reaction mixture is under reduced pressure to remove the pyridine and the residue is purified by silica gel column chromatography to give 828 mg of the captioned compound.

IR(KBr)cm$^{-1}$: 3410, 2920, 2850, 1630, 1490, 1465, 1288, 1208, 1190, 1120, 1050, 785.

NMR(90 MHz, CDCl$_3$) δ: 0.87(3H,t), 1.25(32H,m), 2.63(2H,m), 2.73(3H,s), 3.15–3.55(8H,m), 3.38(3H,s). 3.85(1H,m), 5.09(2H,t), 8.10(2H,t) 8.49(1H,t), 9.42(2H,d).

EXAMPLE 46

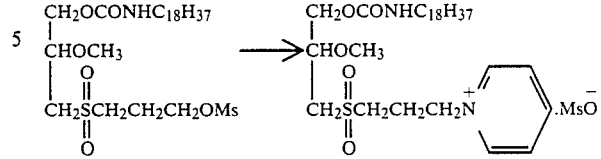

N-[3-((2-Methoxy-3-octadecylcarbamoyloxypropyl)-sulfonyl)propyl]-pyridinium mesylate The captioned compound is obtained in the same manner as that of Example 45 from 3-mesyloxypropyl 2-methoxy-3-octadecylcarbamoyloxypropyl sulfone and pyridine.

IR(KBr)cm$^{-1}$: 3420, 2920, 2850, 1700, 1630, 1525, 1462, 1195, 1110.

NMR(90 MHz, CDCl$_3$) δ: 0.88(3H,t), 1.1–1.7(32H,m), 2.71(3H,s), 2.5–2.8(2H,m), 3.33(3H,s), 3.0–4.4(9H,m). 5.07(2H,t), 6.01(1H,t), 8.08(2H,t) 8.45(1H,t), 9.43(2H,d).

EXAMPLE 47

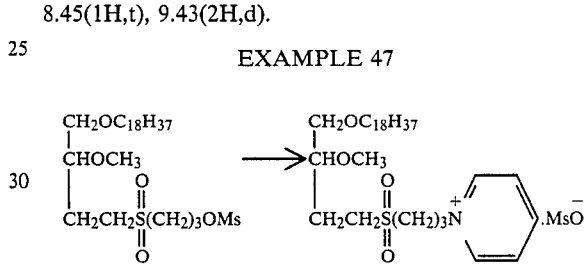

N-[3-((3-Methoxy-4-octadecyloxybutyl)sulfonyl)-propyl]pyridinium mesylate

The captioned compound is obtained in the same manner as that of Example 45 from 3-mesyloxypropyl 3-methoxy-4-octadecyloxybutyl sulfone and pyridine.

IR(KBr)cm$^{-1}$: 3420, 2920, 2850, 1635, 1490, 1468, 1202, 1190, 1122, 1058.

NMR(90 MHz, CDCl$_3$) δ: 0.87(3H,t), 1.25(32H,m), 2.1(2H,m), 2.65(2H,m), 2.73(3H,s), 3.38(3H,s). 3.0–3.5(9H,m), 5.11(2H,t), 8.07(2H,t), 8.43(1H,t), 9.38(2H,d).

EXAMPLE 48

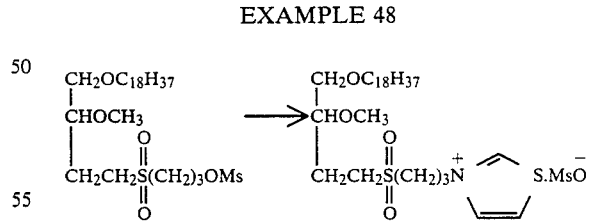

N-[3-((3-Methoxy-4-octadecyloxybutyl)sulfonyl) propyl]thiazolium mesylate

The captioned compound is obtained in the same manner as that of Example 45 from 3-mesyloxypropyl 3-methoxy-4-octadecyloxybutyl sulfone and thiazole.

IR(KBr)cm$^{-1}$: 3420, 2925, 2850, 1550, 1468, 1202, 1190, 1120, 1060.

NMR(90 MHz, CDCl$_3$) δ: 0.87(3H,t), 1.25(32H,m), 2.1(2H,m), 2.6(2H,m), 2.73(3H,s), 3.38(3H,s). 3.0–3.5(9H,m), 5.0(2H,t), 8.13(1H), 8.53(1H), 10.81(1H).

EXAMPLE 49

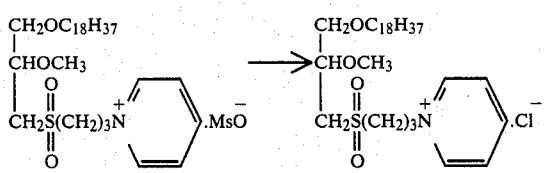

N-[3-((2-Methoxy-3-octadecyloxypropyl)sulfonyl)-propyl]pyridinium chloride

N-[3-((2-Methoxy-3-octadecyloxypropyl)sulfonyl)-propyl]pyridinium mesylate (134 mg) is dissolved in 80% methanol and the solution is treated with anion exchange resin IRA-410 (Cl type). The treated solution is then concentrated under reduced pressure to remove the solvent and the residue is treated with acetone to yield 99 mg of the captioned compound as colorless powder.

IR(KBr)cm$^{-1}$: 2920, 2850, 1632, 1490, 1465, 1288, 1120.

NMR(90 MHz, CDCl$_3$) δ: 0.87(3H,t), 1.25(32H,m), 2.66(2H,m), 3.15–3.60(8H,m), 3.38(3H,s), 3.87(1H,m), 5.25(2H,t), 8.13(2H,t), 8.51(1H,t), 9.65(1H,t).

EXAMPLE 50

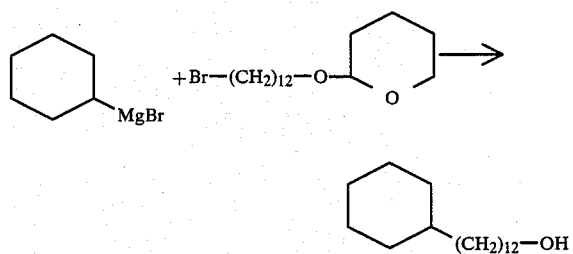

12-Cyclohexyldodecanol

Into 250 ml of tetrahydrofuran (THF) is dissolved 57.8 g of 2-[(12-bromododecyl)oxy]tetrahydro-2H-pyran, to which a solution of 0.35 g of dilithium tetrachlorocuprate in 16 ml of THF is added dropwise at room temperature with stirring under nitrogen streams. To the resulting solution, a solution of 39.6 g of cyclohexylmagnesium bromide in 200 ml of THF is added dropwise while maintaining the reaction temperature at 10°–15° C. Thereafter, the reaction mixture is stirred for 7 hours at room temperature to complete the reaction. The reaction mixture is then acidified with 2N sulfuric acid under ice cooling. The undissolved substances are removed by filtration and the precipitates are washed with ethyl acetate. The THF layer and the ethyl acetate layer are combined and the resulting solution is washed with water, an aqueous sodium bicarbonate solution and then water and is dried. The solvent is removed by distillation under reduced pressure to leave crude [(12-cyclohexyldodecyl)oxy]-tetrahydro-2H-pyran which in turn is dissolved in 450 ml of methanol. Amberlyst ® H-15 (4.5 g) is added to the methanol solution and the mixture is stirred at 45° C. for 2 hours. The resin is then filtered off and the filtrate is concentrated to leave a residue. Purification of the residue by silica gel column chromatography yields 20.6 g of the captioned compound as colorless solids.

IR(KBr)cm$^{-1}$: 3370, 2890, 2840, 1620, 1460, 1450, 1350, 1050, 1030, 720.

NMR(90 MHz, CDCl$_3$) δ: 1.25(26H), 1.47–1.73(7H), 3.47–3.68(2H).

EXAMPLE 51

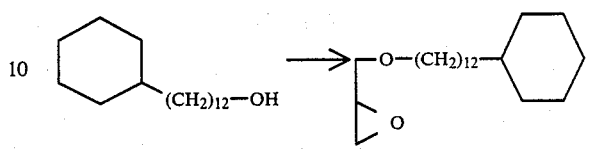

1,2-Epoxy-3-(12-cyclohexyldodecyloxy)propane

A mixture containing 26.5 g of 12-cyclohexyldodecanol, 27.4 g of epichlorohydrin, 52.6 g of a 50% aqueous sodium hydroxide solution, 2.0 g of cetyltrimethylammonium chloride and 300 ml of toluene is stirred at 60° C. for 24 hours. The resulting reaction mixture is then washed with water, dried and concentrated to leave a residue which in turn is purified by silica gel chromatography to obtain 22.8 g of the captioned compound as a colorless oily substance.

IR(Neat)cm$^{-1}$: 2920, 2850, 1450, 1340, 1250, 1110, 910, 840.

NMR(90 MHz, CDCl$_3$) δ: 1.10–1.75(32H), 2.58(1H), 2.78(1H), 3.13(1H), 3.27–3.77(4H).

EXAMPLE 52

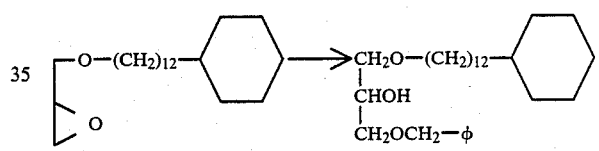

1-Benzyl-3-(12-cyclohexyldodecyl)glycerine

In 100 ml of dimethylsulfoxide is suspended 1.4 g of sodium hydride, to which 9.73 g of benzyl alcohol is added dropwise at room temperature with stirring. After the addition is over, the mixture is gradually heated to 60° C. and stirred at that temperature for 40 minutes. Then, a solution of 9.7 g of 1,2-epoxy-3-(12-cyclohexyldodecyloxy)propane in 50 ml of tetrahydrofuran is added dropwise to the mixture and the resulting mixture is stirred at 60° C. for 2 hours. The thus obtained reaction mixture is then neutralized with dilute hydrochloric acid and extracted with hexane-ethyl acetate (1:1). The extract layer is washed with water, dried and concentrated. The residue is purified by silica gel column chromatography to yield 10.2 g of the captioned compound as an oily substance.

NMR(90 MHz, CDCl$_3$) δ: 0.8–1.9(33H,m), 2.50(1H,d), 3.37–3.60(6H,m), 3.75–4.25(1H,m), 4.63(2H,s) 7.33(5H,s).

EXAMPLE 53

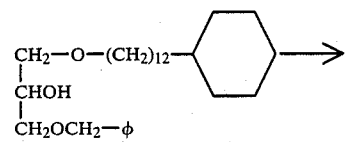

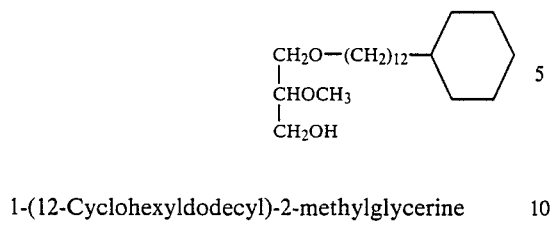

1-(12-Cyclohexyldodecyl)-2-methylglycerine

In 70 ml of tetrahydrofuran is suspended 0.86 g of sodium hydride, to which a solution of 10.2 g of 1-benzyl-3-(12-cyclohexyldodecyl)glycerine in 50 ml of tetrahydrofuran is added dropwise at room temperature with stirring. After 40 minutes stirring at room temperature, 5.11 g of methyl iodide is added and the mixture is further stirred for 2 hours. The solvent is then distilled off under reduced pressure and the residue is extracted with hexane. The extract layer is washed with water, dried and concentrated to obtain crude 1-benzyl-2-methyl-3-(12cyclohexyldodecyl)glycerine which in turn is dissolved in a mixed solvent consisting of 100 ml of ethanol and 30 ml of acetic acid. The solution is shaked in the presence of 10% palladium-carbon under hydrogen streams. The catalyst is removed by filtration and the filtrate is concentrated to obtain 9.6 g of the captioned compound as a crude product.

NMR(90 MHz, CDCl$_3$) δ: 0.7–1.9(33H,m), 2.2(1H,br,s), 3.3–3.8(7H,m), 3.43(3H,s).

EXAMPLE 54

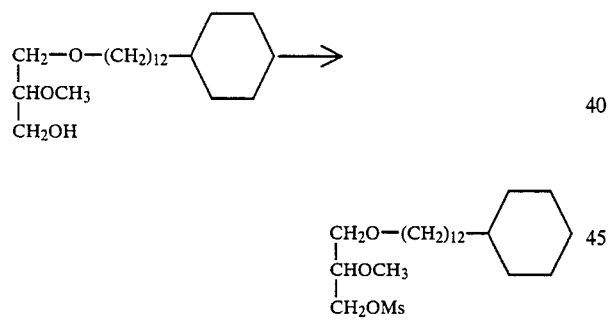

2-Methoxy-3-(12-cyclohexyldodecyloxy)propyl methanesulfonate

To 100 ml of dichloromethane are added 10.8 g of 1-(12-cyclohexyldodecyl)-2-methylglycerine and 4.42 ml of triethylamine, to which 3.64 g of methanesulfonyl chloride is added dropwise with stirring under ice cooling. Then, the mixture is stirred at room temperature for 2 hours to complete the reaction. The reaction mixture is washed with water, an aqueous sodium bicarbonate solution and water, and dried. The solvent is removed by distillation to leave 10.42 g of the captioned compound.

IR(KBr)cm$^{-1}$: 2925, 2850, 1345, 1170, 1125, 985, 965, 860.

NMR(90 MHz, CDCl$_3$) δ: 0.7–1.9(33H,m), 3.03(3H,s), 3.47(3H,S), 3.3–3.7(5H,m), 4.1–4.5(2H,m).

EXAMPLE 55

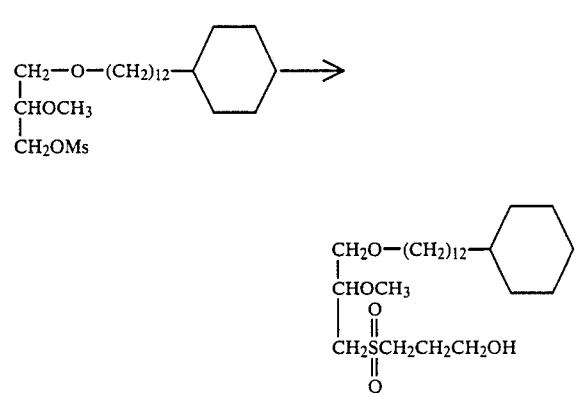

2-Methoxy-3-(12-cyclohexyldodecyloxy)propyl 3-hydroxypropyl sulfone

To 90 ml of a methanol solution of sodium methoxide (1 M solution) are added 8.82 g of 3-mercaptopropanol and 1.5 g of sodium borohydride, to which a solution of 10.4 g of 2-methoxy-3-(12-cyclohexyldodecyloxy)propyl methanesulfonate in 120 ml of tetrahydrofuran is added dropwise at room temperature with stirring under nitrogen streams. The reaction mixture, after being stirred at room temperature overnight, is acidified with hydrochloric acid. The methanol is distilled off under reduced pressure and the residue is extracted with hexane. The extract layer is washed with water, dried and concentrated to leave 10.2 g of crude 2-methoxy-3-(12-cyclohexyldodecyloxy)propyl 3-hydroxypropyl sulfide. The crude sulfide is dissolved in 250 ml of dichlromethane, to which 10.0 g of m-chloroperbenzoic acid is added little by little at room temperature with stirring. After 3 hour-stirring at room temperature, the undissolved substances are removed by filtration and the filtrate is washed with an aqueous sodium hydrogensulfite solution, an aqueous sodium bicarbonate solution and water, and dried. The solvent is then distilled off under reduced pressure to leave a residue which in turn is purified by silica gel column chromatography, thereby yielding 8.9 g of the captioned compound.

IR(Neat)cm$^{-1}$: 3400, 2925, 2850, 1445, 1295, 1210.

NMR(90 MHz, CDCl$_3$) δ: 0.7–1.9(33H,m), 1.9–2.25(2H,m), 3.43(3H,S), 3.15–3.6(9H,m), 3.65–4.0(2H,m).

EXAMPLE 56

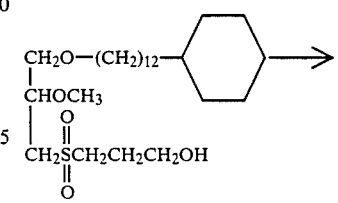

-continued

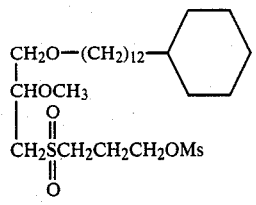

3-Mesyloxypropyl 2-methoxy-3-(12-cyclohexyldodecyloxy)propyl sulfone

In 100 ml of dichloromethane are dissolved 8.9 g of 2-methoxy-3-(12-cyclohexyldodecyloxy)propyl 3-hydroxypropyl sulfone and 3.7 ml of triethylamine, to which 3.0 g of methanesulfonyl chloride is added dropwise with stirring under ice cooling. After 2 hours stirring at room temperature, the reaction solution is washed with water, an aqueous sodium bicarbonate solution and water, and dried. The solvent is then distilled off under reduced pressure to leave 10.4 g of the captioned compound.

IR(Neat)cm$^{-1}$: 2920, 2850, 1465, 1445, 1350, 1170, 1110.

NMR(90 MHz, CDCl$_3$) δ: 0.7–1.9(33H,m), 2.1–2.45(2H,m), 2.973H,S), 3.40(3H,S), 3.05–3.65(8H,m), 3.75–3.95(1H,m), 4.33(2H,t).

EXAMPLE 57

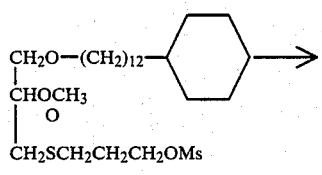

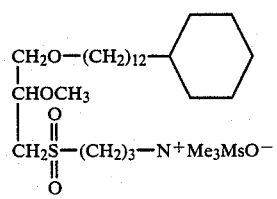

3-[(3-(12-Cyclohexyldodecyloxy)-2-methoxypropyl)-sulfonyl]propyltrimethylammonium mesylate In 50 ml of toluene containing 10 g of trimethylamine is dissolved 5.4 g of 3-mesyloxypropyl 2-methoxy-3-(12-cyclohexyldodecyloxy)propyl sulfone, and the mixture is stirred at room temperature for 5 days. The reaction mixture is then concentrated to dryness and the residue is purified by silica gel column chromatography to obtain 3.17 g of the captioned compound.

IR(KBr)cm$^{-1}$: 3420, 2920, 2850, 1480, 1445, 1290, 1210, 1190, 1110, 1060.

NMR(90 MHz, CDCl$_3$) δ: 0.9–1.8(33H,m), 2.2–2.6(2H,m), 2.70(3H,S), 3.2–3.6(8H,m), 3.33(9H,s), 3.43(3H,s), 3.65–4.0(3H,m).

EXAMPLE 58

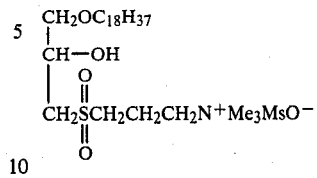

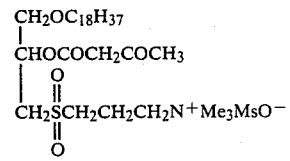

3-[(2-Acetoacetoxy-3-octadecyloxypropyl)sulfonyl]-propyltrimethylammonium mesylate In a mixed solvent consisting of 5 ml of pyridine and 20 ml of dichloromethane is dissolved 2.35 g of 3-[(2-hydroxy-3-octadecyloxypropyl)sulfonyl]propyltrimethylammonium mesylate, to which 2.5 ml of diketene is added dropwise with stirring under ice cooling. Thereafter, the mixture is stirred at room temperature for 5 hours, to which is then added 3 ml of methanol. The solvent is distilled off under reduced pressure to leave a residue which in turn is purified by silica gel column chromatography to yield 0.5 g of the captioned compound.

IR(KBr)cm$^{-1}$: 3430, 2920, 2850, 1745, 1720, 1620, 1465, 1190, 1125, 1060.

NMR(90 MHz, CDCl$_3$) δ: 0.87(3H,t), 1.25(32H,m), 2.26(3H,S), 2.1–2.5(2H,m), 2.67(3H,s), 3.27(9H,s), 3.0–3.9(12H,m), 5.53(1H,m).

EXAMPLE 59

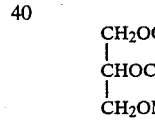

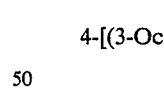

4-[(3-Ocatadecyloxy-2-methoxypropyl)sulfonyl]-butanol

To 40 ml of a methanol solution of sodium methoxide (1 M solution) are added 3.1 g of 4-mercaptobutanol and 0.5 g of sodium borohydride, to which is added dropwise a solution of 4.36 g of 2-methoxy-3-octadecyloxypropyl methanesulfonate in 40 ml of tetrahydrofuran at room temperature with stirring. The mixture is stirred at room temperature for 14 hours and then at 40° C. for 1.5 hours. The solvent is distilled off under reduced pressure and the residue is acidified with hydrochloric acid and extracted with hexane. The extract layer is washed with water, dried and concentrated to leave crude 2-methoxy-3-octadecyloxypropyl 4-hydroxybutyl sulfide. This sulfide is dissolved in 75 ml of dichloromethane, to which 7.6 g of m-chloroperbenzoic acid is added little by little at room temperature with stirring. The mixture is then stirred at room temperature for 1 hour and is filtered to remove precipitates. The filtrate is washed with an aqueous sodium sulfite solution, an aqueous sodium bicarbonate solution and water, dried and concentrated to leave a residue which in turn is purified by silica gel column chromatography to obtain 2.5 g of the captioned compound.

IR(KBr)cm$^{-1}$: 3450, 2920, 2850, 1465, 1380, 1290, 1115, 968.

NMR(90 MHz, CDCl$_3$) δ: 0.87(3H,t), 1.25(30H,m), 1.45–2.1(6H,m), 2.93–3.8(10H,m) 3.43(3H,s), 3.90(1H,m),

EXAMPLE 60

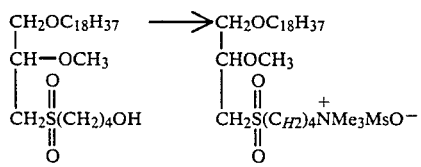

4-[(3-Octadecyloxy-2-methoxypropyl)sulfonyl]butyl-trimethylammonium mesylate

In 50 ml of dichloromethane is dissolved 2.5 g of 4-[(3-octadecyloxy-2-methoxypropyl)sulfonyl]butanol, to which 0.78 g of methanesulfonyl chloride and 0.95 ml of triethylamine are added dropwise with stirring under ice cooling. After being stirred at room temperature for 40 minutes, the mixture is washed with water, an aqueous sodium bicarbonate solution and water, and dried. The solvent is distilled off under reduced pressure to leave 2.76 g of 4-mesyloxybutyl 3-octadecyloxy-2-methoxypropyl sulfone. This is dissolved in 40 ml of toluene containing 8 g of trimethylamine, and the solution is stirred at room temperature for 40 hours. The reaction mixture is concentrated and reprecipitated from chloroform-acetone to give 2.1 g of the captioned compound.

IR(KBr)cm$^{-1}$: 3420, 2920, 2850, 1465, 1292, 1208, 1190, 1120, 1060.

NMR(90 MHz, CDCl$_3$) δ: 0.87(3H,t), 1.25(32H,m), 1.96(4H,m), 2.69(3H,s), 3.30(9H,s) 3.45(3H,s), 3.0–3.75(10H,m), 3.88(1H,quint).

EXAMPLE 61

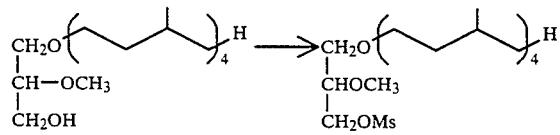

2-Methoxy-3-(3,7,11,15-tetramethylhexadecyloxy)propyl methanesulfonate

In 100 ml of ethyl acetate are dissolved 9.21 g of 2-methoxy-3-(3,7,11,15-tetramethylhexadecyloxy)-propanel and 4.66 ml of triethylamine, to which 10.1 ml of methanesulfonyl chloride is added dropwise with stirring under ice cooling. The stirring is continued for 30 minutes under ice cooling and then at room temperature for 2 hours. The reaction mixture is washed successively with water, dilute hydrochloric acid, water, an aqueous sodium bicarbonate solution and water. After drying, the solvent is distilled off under reduced pressure to leave 9.8 g of the captioned compound.

IR(Neat)cm$^{-1}$: 2910, 2850, 1460, 1360, 1180.

NMR(90 MHz, CDCl$_3$) δ: 0.7–1.7(39H,m), 3.01(3H,s), 3.3–3.7(5H,m), 3.45(3H,s), 4.30(2H,m).

EXAMPLE 62

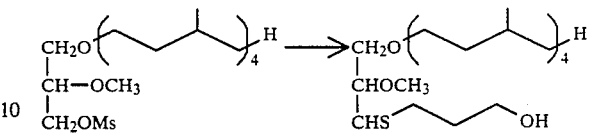

2-Methoxy-3-(3,7,11,15-tetramethylhexadecyloxy)propyl 3-hydroxypropyl sulfide

To 30 ml of teterahydrofuran are added 11.8 ml of a methanol solution of sodium methoxide (28% solution), 0.57 g of sodium borohydride and 4.14 g of 3-mercaptopropanol, to which is added dropwise a solution of 6.97 g of 2-methoxy-3(3,7,11,15-tetramethylhexadecyloxy)-propyl methanesulfonate in 50 ml of tetrahydrofuran at room temperature with stirring under nitrogen streams. Thereafter, the reaction mixture is stirred at room temperature for 16 hours. The solvent is distilled off under reduced pressure and the residue is extracted with hexane. The extract layer is washed successively with water, dilute hydrochloric acid, water, an aqueous sodium bicarbonate solution and then with water. After drying, the solvent is distilled off under reduced pressure to leave 6.67 g of the captioned compound as an oily substance.

IR(Neat)cm$^{-1}$: 3400, 2910, 2850, 1465, 1380, 1120.

NMR(90 MHz, CDCl$_3$) δ: 0.7–1.7(39H,m), 1.63(1H,t), 1.84(2H,m), 2.62–2.77(4H,m), 3.3–3.6(5H,m), 3.39(3H,s), 3.73(2H,m).

EXAMPLE 63

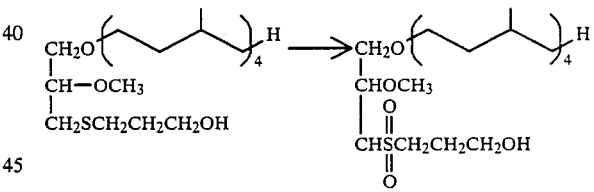

3-[(2-methoxy-3-(3,7,11,15-tetramethylhexadecyloxy)-propyl)sulfonyl]propanol

In 150 ml of dichloromethane is dissolved 6.66 g of 2-methoxy 3-(3,7,11,15-tetramethylhexadecyloxy)propyl 3-hydroxypropyl sulfide, to which 7.38 g of m-chloroperbenzoic acid is added little by little with stirring under ice cooling. After 2 hours stirring at room temperature, the undissolved substances are removed by filtration and the filtrate is washed with water, an aqueous sodium bisulfite solution, water, an aqueous sodium bicarbonate solution and water. After drying, the solvent is distilled off to leave a residue which in turn is purified by silica gel column chromatography to obtain 6.48 g of the captioned compound as an oily substance.

IR(Neat)cm$^{-1}$: 3450, 2910, 2850, 1465, 1380, 1300, 1125, 1017.

NMR(90 MHz, CDCl$_3$) δ: 0.7–1.8(41H,m), 1.8(1H), 2.0–2.3(4H,m), 3.0–3.6(5H,m), 3.44(3H,s), 3.7–4.2(3H,m).

EXAMPLE 64

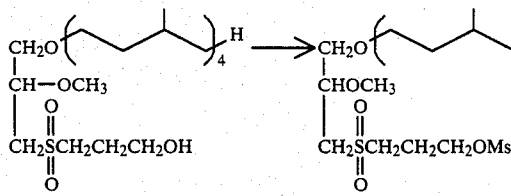

3-Mesyloxypropyl 2-methoxy-3-(3,7,11,15-tetramethylhexadecyloxy)-propyl sulfone To 100 ml of ethyl acetate are added 4.5 g of 3-[(2-methoxy-3-(3,7,11,15-tetramethylhexadecyloxy)-propyl)sulfonyl]propanol and 1.54 ml of triethylamine, to which is further added 0.85 ml of methanesulfonyl chloride dropwise at room temperature with stirring. After being stirred at room temperature for 3 hours, the reaction mixture is washed with water, dilute hydrochloric acid, an aquoues sodium bicarbonate and water. After drying, the solvent is distilled off to leave 5.16 g of the captioned compound as an oily substance.

IR(Neat)cm$^{-1}$: 2920, 2850, 1460, 1355, 1240, 1180, 1120.

NMR(90 MHz, CDCl$_3$) δ: 0.7–1.8(41H,m), 2.33(4H,m), 3.02(3H,s), 3.1–3.6(5H,m), 3.44(3H,s), 3.8–4.1(1H,m). 4.37(2H,t).

EXAMPLE 65

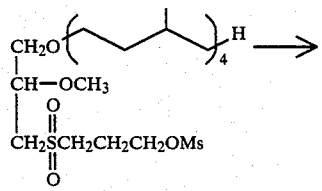

3-[(2-Methoxy-3-(3,7,11,15-tetramethylhexadecyloxy)-propyl)sulfonyl]propyltrimethylammonium mesylate In 20 ml of toluene containing 4 g of trimethylamine is dissolved 3.1 g of 3-mesyloxypropyl 2-methoxy-3-(3,7,11,15-tetramethylhexadecyloxy)propyl sulfone, and the mixture is stirred at room temperature for 3 days. The reaction mixture is concentrated under reduced pressures to leave a residue which in turn is purified by silica gel column chromatography to yield 2.49 g of the captioned compound.

IR(KBr)cm$^{-1}$: 2920, 2850, 1460, 1375, 1290, 1200, 1110, 1050.

NMR(90 MHz, CDCl$_3$) δ: 0.7–1.8(41H,m), 2.2–2.6(4H,m), 2.69(3H,s), 3.1–4.0(5H,m), 3.34(9H,s), 3.46(3H,s).

EXAMPLE 66

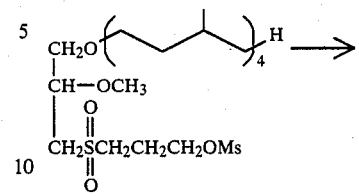

N-[3-[(2-methoxy-3-(3,7,11,15-tetramethylhexadecyloxy)propyl)sulfonyl]propyl]morpholinium hydrochloride 1.2 g of 3-mesyloxypropyl 2-methoxy-3-(3,7,11,15-tetramethylhexadecyloxy)propyl sulfone is added to 2 ml of morpholine, and the mixture is stirred for 2 hours at 100° C. Water is added to the solution, and it is extracted with ethyl acetate. The extract layer is washed with an aqueous sodium bicarbonate solution and water, and dried. The solvent is distilled off under reduced pressure to leave a residue which in turn is purified by silica gel column chromatography and treated with methanol-hydrogen chloride to yield 0.89 g of the captioned compound.

IR(KBr)cm$^{-1}$: 2920, 2850, 2300–2700, 1455, 1375, 1280, 1120.

NMR(90 MHz, CDCl$_3$) δ: 0.7–1.7(39H,m), 2.4–2.7(2H,m), 3.0–4.3(19H,m), 3.41(3H,m).

TEST EXAMPLE 1

ICR mice (a group consisting of five mice) were inoculated intraperitoneally with $1 \times 10^5$ Sarcoma 180 cells per mouse, and then given intraperitoneally 0.33 mg/mouse of the compound prepared in the present invention dissolved in physiological saline, three times in total, 1 hour, 1 day and 2 days after the inoculation. Also, the control compound [III] was given to mice under the same conditions. Shown in Table 1 are the life-span prolongation ratio against the control group not treated with drug (only related to mice of survival days less than 60 days) and the number of survived mice on the 60th day after the initiation of the test.

TABLE 1

| Compound Tested | Life-Span Prolongation Ratio(T/C, %) | 60th day: No. of survivors/ No. of tested mice |
|---|---|---|
| Compound of Example 30 | 350 | 0/5 |
| Compound of Example 37 | 326 | 0/5 |
| Compound of Example 31 | 273 | 0/5 |
| Compound of Example 36 | 242 | 1/5 |
| Compound [III] | 162 | 0/5 |
| Control | 100 | 0/5 |

TEST EXAMPLE 2

C3H/He mice (a group consisting of five mice) were inoculated intraperitoneally with $1\times10^4$ MM46 cells per mouse, and each mouse was intraperitoneally given 0.25 mg of drug for consecutive 4 days, starting from the second day after the inoculation. Shown in Table 2 are the life-span prolongation ratio ragarding the died mice in the group treated with drug against those in the control group not treated with drug (only related to mice of survival days less than 60 days) and the number of survived mice on the 60th day after the inoculation of MM46.

TABLE 2

| Compound Tested | Life-Span Prolongation Ratio(T/C, %) | No. of survivors/ No. of tested mice |
|---|---|---|
| Compound of Example 30 | 225 | 4/5 |
| Compound [III] | 155 | 0/5 |
| Control | 100 | 0/5 |

TEST EXAMPLE 3

Proliferation inhibiting activity ($IC_{50}$) of the compound of the present invention againsts human myelogenic leukaemia cells HL-60 was measured according to the method of R. Gallo et al [Blood, vol. 54, 713(1979)]. The results are shown in Table 3.

TABLE 3

| Compound Tested (Example No.) | Inhibitory concentration against HL-60($IC_{50}$, μg/ml) |
|---|---|
| 30 | 1.25 |
| 31 | 5 |
| 36 | 2.5 |
| 37 | 2.5 |
| 38 | 5 |
| 45 | 1.25 |
| 47 | 1.25 |
| 48 | 2.5 |

TEST EXAMPLE 4

PAF Inhibiting Activity

PAF inhibiting Activity in Platelet Aggregation

[Test Method and Results]

Using a syringe containing 3.15% citric acid (1 part per 9 parts of blood) as a blood coagulation inhibitor, blood was taken from male rabbit. The blood was then centrifuged at 1000 rpm at room temperature for 10 minutes to obtain a platelet rich plasma (PRP). This PRP was further centrifuged at 1400 rpm for 15 minutes to obtain a platelet pellet. The pellet was suspended in $Ca^{++}$-free Tyrode containing 0.25% gelatin to obtain washed PRP. This PRP (250 μl) was stirred at 37° C. for 2 minutes, to which was then added 25 μl of a 0.2–0.5 mM $Ca^{++}$ solution. After this mixture had been stirred for 30 seconds, a medicine to be tested was added thereto. After 2 minutes stirring, $3\times10^{-7}$ M of PAF was added to the mixture. Pellet aggregation was measured by means of a platelet aggregometer (manufactured by Rika Denki, Japan). The activity of the test samples was determined in terms of an inhibiting ratio relative to the maximum transmittance (maximum aggregation ratio) of control PRP by PAF.

The results are shown in Table 4.

TABLE 4

| Compound Tested (Example No.) | Inhibiting Ratio Medicine Concentration | |
|---|---|---|
| | $3\times10^{-6}$ M | $3\times10^{-5}$ M |
| 31 | 100 | 100 |
| 45 | 82 | 100 |
| 46 | 100 | 100 |
| 47 | 73 | 100 |
| 48 | 65 | 100 |

The compound or salt thereof according to the present invention is a novel substance and has both anti-tumor activity and platelet activating factor-inhibiting property. Thus, it is effective as a potent anti-tumor agent for tumor-bearing animals because of its increased anti-tumor activity inclusive of cytotoxicity against tumor cells and as an agent for preventing or curing circulatory trouble diseases or allergic diseases induced by PAF because of its PAF inhibiting activity.

We claim:

1. A compound of the general formula:

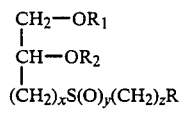

wherein $R_1$ represents a higher alkyl group of 14 to 20 carbon atoms or an N-(higher alkyl)carbamoyl group in which the higher alkyl group contains 14 to 20 carbon atoms, $R_2$ represents an alkyl group of 1–4 carbon atoms, an alkanoyl group having 3 or 4 carbon atoms, an acetoacetyl group, an N-(alkyl)carbamoyl group, wherein the alkyl group contains 1 to 4 carbon atoms, an N-(alkyl)thiocarbamoyl group wherein the alkyl group contains 1 to 4 carbon atoms, or a benzyl group, R represents a primary, secondary or tertiary amino group or a quaternary ammonium group, X is 1 or 2, y is 0, 1 or 2, and z is an integer of 2 to 10, or a pharmaceutically acceptable salt thereof.

2. A compound or a pharmaceutically acceptable salt thereof according to claim 1, wherein $R_1$ is octadecyl, tetradecyl, 12-cyclohexyldodecyl or 3,7,11,15-tetramethyl hexadecyl group.

3. A compound or a pharmaceutically acceptable salt thereof according to claim 1, wherein $R_1$ is N-octadecylcarbamoyl group.

4. A compound or a pharmaceutically acceptable salt thereof according to claim 1, wherein $R_2$ is an alkyl group having 1–4 carbon atoms.

5. A compound or a pharmaceutically acceptable salt thereof according to claim 4, wherein $R_2$ is methyl.

6. A compound or a pharmaceutically acceptable salt thereof according to claim 1, wherein $R_2$ is an N-($C_{1-4}$ alkyl)carbamoyl group.

7. A compound or a pharmaceutically acceptable salt thereof according to claim 1, wherein $R_2$ is N-($C_{1-4}$ alkyl)thiocarbamoyl group.

8. A compound or a pharmaceutically acceptable salt thereof according to claim 1, wherein R is a primary, secondary or tertiary amino group represented by the formula:

wherein $R_3$ and $R_4$ are independently hydrogen or lower alkyl of 1 to 5 carbon atoms, or $R_3$ and $R_4$ form a cyclic amino group together with the adjacent nitrogen atom.

9. A compound or a pharmaceutically acceptable salt thereof according to claim 8, wherein R is dimethylamino.

10. A compound or a pharmaceutically acceptable salt thereof according to claim 8, where

is a cyclic amino group which is five or six membered group, which may be substituted by $C_{1-4}$-alkyl, hydroxyl, hydroxyethyl, aminoethyl, carbamoyl or ureido.

11. A compound or a pharmaceutically acceptable salt thereof according to claim 1, wherein R is a quaternary ammonium group represented by the formula:

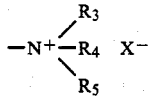

wherein $R_3$, $R_4$ and $R_5$ are independently hydrogen or a lower alkyl group of 1 to 5 carbon atoms or $R_3$, $R_4$ and $R_5$ form a cyclic ammonio group together with the adjacent nitrogen atom, and X is a pharmacologically acceptable anion.

12. A compound or a pharmaceutically acceptable salt thereof according to claim 11, wherein R is trimethyl ammonium mesylate or trimethyl ammonium iodide.

13. A compound or a pharmaceutically acceptable salt thereof according to claim 1, wherein

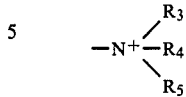

is a cyclic ammonio group which is five or six membered group, which may be substituted by $C_{1-4}$-alkyl, hydroxyl, hydroxyethyl, aminoethyl, carbamoyl or ureido.

14. A compound or a pharmaceutically acceptable salt thereof according to claim 11, wherein R is pyridinium mesylate, thiazolium mesylate, pyridinium chloride or morpholinium chloride.

15. A salt of claim 1, which is 3-[(2-methoxy-3-octadecyloxypropyl)sulfonyl]propyltrimethylammonium mesylate.

16. A salt of claim 1, which is 6-[(2-methoxy-3-octadecyloxypropyl)sulfonyl]hexyltrimethylammonium mesylate.

17. A salt of claim 1, which is 3-[(3-methoxy-4-octadecyloxypropyl)sulfonyl]propyltrimethylammonium mesylate.

18. A salt of claim 1, which is 3-[(3-methoxy-4-octadecyloxypropyl)sulfinyl]propyltrimethylammonium mesylate.

19. A salt of claim 1, which is 3-[(2-methoxy-3-octadecyloxypropyl)thio]propyltrimethylammonium mesylate.

20. A salt of claim 1, which is N-[(3-((2-methoxy-3-octadecyloxypropyl)sulfonyl)propyl]pyridinium mesylate.

21. A salt of claim 1, which is N-[(3-((2-methoxy-3-octadecylcarbamoyloxypropyl)sulfonyl)propyl]-pyridinium mesylate.

22. A salt of claim 1, which is N-[(3-((3-methoxy-4-octadecyloxypropyl)sulfonyl)propyl]pyridinium mesylate.

23. A salt of claim 1, which is N-[(3-((3-methoxy-4-octadecyloxypropyl)sulfonyl)propyl]thiazolium mesylate.

* * * * *